(12) United States Patent
Summers et al.

(10) Patent No.: US 10,590,061 B2
(45) Date of Patent: *Mar. 17, 2020

(54) SYSTEM AND METHODS FOR MAKING BIOPRODUCTS

(71) Applicant: Benefuel, Inc., Des Moines, IA (US)

(72) Inventors: William A. Summers, Des Moines, IA (US); Rebecca Williams, Aberdeen, MS (US); Danny Gulledge, Montrose, AR (US); Robert Barrie Tripp, Coppell, TX (US)

(73) Assignee: BENEFUEL, INC., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/948,838

(22) Filed: Apr. 9, 2018

(65) Prior Publication Data

US 2018/0319733 A1 Nov. 8, 2018

Related U.S. Application Data

(63) Continuation of application No. 14/518,559, filed on Oct. 20, 2014, now Pat. No. 10,023,523, which is a continuation of application No. 13/414,484, filed on Mar. 7, 2012, now Pat. No. 8,962,873.

(60) Provisional application No. 61/451,037, filed on Mar. 9, 2011, provisional application No. 61/451,040, filed on Mar. 9, 2011, provisional application No. 61/451,043, filed on Mar. 9, 2011.

(51) Int. Cl.
| | |
|---|---|
| *C07C 67/293* | (2006.01) |
| *C11C 3/10* | (2006.01) |
| *B01J 14/00* | (2006.01) |
| *B01J 19/00* | (2006.01) |

(52) U.S. Cl.
CPC ............. *C07C 67/293* (2013.01); *B01J 14/00* (2013.01); *B01J 19/0006* (2013.01); *C11C 3/10* (2013.01); *Y02E 50/13* (2013.01)

(58) Field of Classification Search
CPC ................................................... C07C 67/293
USPC ......................................................... 554/168
See application file for complete search history.

(56) References Cited

U.S. PATENT DOCUMENTS

| | | | |
|---|---|---|---|
| 3,278,457 | A | 10/1966 | Milgrom |
| 5,482,908 | A | 1/1996 | Le-Khac |
| 5,525,126 | A | 6/1996 | Basu et al. |
| 5,536,883 | A | 7/1996 | Le-Khac |

(Continued)

FOREIGN PATENT DOCUMENTS

| | | |
|---|---|---|
| EP | 1593732 A1 | 11/2005 |
| JP | 2001-17862 A | 1/2001 |

(Continued)

OTHER PUBLICATIONS

Nakagaki et al. "Use of anhydrous sodium molybdate as an efficient heterogeneous catalyst for soybean oil methanolysis," Applied Catalysis A: General, 2008, pp. 267-274; Elsevier.

(Continued)

*Primary Examiner* — Deborah D Carr
(74) *Attorney, Agent, or Firm* — Husch Blackwell LLP

(57) ABSTRACT

Processes for continuous preparation of bioproducts are described herein. The processes include contacting fatty acid glycerides with alcohols in the presence of an acidic heterogeneous catalyst and separating the fatty acid alkyl esters from the reaction products.

18 Claims, 3 Drawing Sheets

(56) References Cited

U.S. PATENT DOCUMENTS

| | | | |
|---|---|---|---|
| 5,578,090 | A | 11/1996 | Bradin |
| 5,713,965 | A | 2/1998 | Foglia et al. |
| 5,908,946 | A | 6/1999 | Stern et al. |
| 6,015,440 | A | 1/2000 | Noureddini |
| 6,147,196 | A | 11/2000 | Stern et al. |
| 6,262,285 | B1 | 7/2001 | Mcdonald |
| 6,383,970 | B1 | 5/2002 | Mimura et al. |
| 6,398,707 | B1 | 6/2002 | Wu et al. |
| 6,399,800 | B1 | 6/2002 | Haas et al. |
| 6,479,689 | B1 | 11/2002 | Tojo et al. |
| 6,489,496 | B2 | 12/2002 | Barnhorst et al. |
| 6,624,286 | B2 | 9/2003 | Hofmann et al. |
| 6,642,399 | B2 | 11/2003 | Boocock |
| 6,696,583 | B2 | 2/2004 | Koncar et al. |
| 6,712,867 | B1 | 3/2004 | Boocock |
| 6,768,015 | B1 | 7/2004 | Luxem et al. |
| 6,822,105 | B1 | 11/2004 | Luxem et al. |
| 6,835,858 | B1 | 12/2004 | De Jonge et al. |
| 6,855,838 | B2 | 2/2005 | Haas et al. |
| 6,878,837 | B2 | 4/2005 | Bournay et al. |
| 6,960,672 | B2 | 11/2005 | Nakayama et al. |
| 6,960,972 | B2 | 11/2005 | Nakamura et al. |
| 7,122,688 | B2 | 10/2006 | Lin et al. |
| 7,211,681 | B2 | 5/2007 | Furuta |
| 7,312,355 | B2 | 12/2007 | Coma Canos et al. |
| 7,482,480 | B2 | 1/2009 | Srinivas et al. |
| 7,531,688 | B2 | 5/2009 | Fleisher et al. |
| 7,754,643 | B2 | 7/2010 | Srinivas et al. |
| 7,812,187 | B2 | 10/2010 | Kawashima et al. |
| 7,842,653 | B2 | 11/2010 | Srinivas et al. |
| 8,124,801 | B2 | 2/2012 | Srinivas et al. |
| 8,962,873 | B2 | 2/2015 | Summers et al. |
| 2002/0010359 | A1 | 1/2002 | Kaita et al. |
| 2003/0004363 | A1 | 1/2003 | Koncar |
| 2003/0065202 | A1 | 4/2003 | Goto et al. |
| 2004/0044240 | A1 | 3/2004 | Grosch et al. |
| 2005/0027137 | A1 | 2/2005 | Hooker |
| 2005/0266139 | A1 | 12/2005 | Lacome et al. |
| 2006/0014974 | A1* | 1/2006 | Bournay ............ C07C 29/1285 554/174 |
| 2007/0004599 | A1 | 1/2007 | Srinivas et al. |
| 2007/0083056 | A1 | 4/2007 | Srinivas et al. |
| 2007/0083062 | A1 | 4/2007 | Srinivas et al. |
| 2007/0093380 | A1 | 4/2007 | Srinivas et al. |
| 2007/0167642 | A1 | 7/2007 | Oku et al. |
| 2007/0282118 | A1 | 12/2007 | Gupta et al. |
| 2008/0110082 | A1 | 5/2008 | Maliszewski et al. |
| 2009/0069586 | A1* | 3/2009 | Oku ....................... B01J 21/063 554/170 |
| 2009/0326252 | A1* | 12/2009 | Srinivas .................. B01J 23/28 554/157 |

FOREIGN PATENT DOCUMENTS

| | | |
|---|---|---|
| JP | 2003-55299 | 2/2003 |
| JP | 2003055299 | 2/2003 |
| WO | 200005327 | 2/2000 |
| WO | 2004048311 | 6/2004 |
| WO | 2004085583 | 10/2004 |
| WO | 2008122790 | 10/2008 |
| WO | 2009158379 | 12/2009 |
| WO | 2012122197 | 9/2012 |

OTHER PUBLICATIONS

Sunita et al. "Synthesis of biodiesel over zirconia-supported isopoly and heteropoly tungstate catalysts," Catalysis Communications, Aug. 19, 2007, pp. 696-702; Elsevier.

Alsalme et al. "Heteropoly acids as catalysts for liquid-phase esterification and transesterification," Applied Catalysis A: General, Jul. 31, 2008, pp. 170-175; Elsevier.

Pesaresi et al. "Cs-doped H4SiW12O40 catalysts for biodiesel applications," Applied Catalysis A: General, Mar. 13, 2009, pp. 50-58; Elsevier.

Zieba et al. Methanolysis of Castor Oil Catalysed by Solid Potassium and Cesium Salts of 12-Tungstophosphoric Acid, Catalysis Letters, Oct. 7, 2008, pp. 183-194; Springer.

Cao et ai. "Biodiesel Production From High Acid Value Waste Frying Oil Catalyzed by Superacid Heteropolyacid" Biotechnology and Bioengineering, Mar. 7,2008, pp. 93-100; Wiley InterScience.

Caetano et al. "Esterification of free fatty acids with methanol using heteropolyacids immobilized on silica," Catalysis Communications, Mar. 25, 2008; Elsevier.

Cardoso et at, "Investigation on the Esterification of Fatty Acids Catalyzed by the H3PW12O40 heteropolyacid," J. Am. Oil Chem. Soc., Mar. 26, 2008, pp. 555-560: Springer, AOCS press.

Narasimharao, K. et al. "Structure-activity relations in Cs-doped heteropolyacid catalysts for biodiesel production," Journal of Catalysis, Apr. 25, 2007, pp. 226-234; Elsevier.

Chai et al. "Transesterification of Vegetable Oil to Biodiesel using a Heteropolyacid Solid Catalyst," Adv. Synth. Catal., 2007, pp. 1057-1065; Wiley InterScience.

Rao et al. "Zirconium phosphate supported tungsten oxide solid acid catalysts for the esterification of palmitic acid," Green Chemistry, Jul. 12, 2006, pp. 790-797; The Royal Society of Chemistry.

Lotero et al., "The Catalysis of Biodiesel Synthesis," Catalysis, 2006, pp. 41-83;The Royal Society of Chemistry.

Kim et al., "Transesterification of vegetable oil to biodiesel using heterogeneous base catalyst," Catalysis Today, Jul. 30, 2004, pp. 315-320; Elsevier.

Watkins et al. "Li—CaO catalysed tri-glyceride transesterification for biodiesel applications," Green Chem, Jul. 5, 2004, pp. 335-340; The Royal Society of Chemistry.

Tesser et al. "Kinetics of Oleic Acid Esterification with Methanol in the Presence of Triglycerides," Ind. Eng. Chem. Res. Sep. 17, 2005, pp. 7968-7982.; American Chemical Society.

Mbaraka et al. "Design of multifunctionalized mesoporous silicas for esterifcation," Journal of Catalysis, Dec. 23, 2004, pp. 365-373; Elsevier.

Schuchardt et al. "Transesterification of soybean oil catalyzed by alkylguanidines heterogenized on different substituted polystyrenes," Journal of Molecular Catalysis A: General, Jan. 2, 1996, pp. 37-44; Elsevier.

Noureddini et al, "A Continuous Process for the Conversion of Vegetable Oils into Methyl Esters of Fatty Acids," Journal Am. Oil Chem. Soc., 1998, pp. 1775-1783; AOCS press.

Leclercq et al. "Transesterifcation of Rapeseed Oil in the Presence of Basic Zeolites and Related Solid Catalysts," J. Am. Oil Chem. Soc., 1998, pp. 1161-1165; AOCS press.

Lopez et al., "Transesterification of triacetin with methanol on solid acid and base catalysts," Applied Catalysis A: General, Sep. 22, 2005, pp. 97-105; Elsevier.

Kiss et al, "Solid Acid Catalysts for Biodiesel Production—Towards Sustainable Energy," Adv. Synth. Catalysis, 2006, pp. 75-81, Wiley InterScience.

Suppes et al. "Transeterification of soybean oil with zeolite and metal catalysts," Applied Catalysis A: General, 2004, pp. 213-223; Elsevier.

Bancquart et al. "Glycerol transesterification with methyl stearate over solid basic catalysts I. Relationship between activity and basicity," Applied Catalysis A: General, 2001, pp. 1-11; Elsevier.

Gryglewicz, "Rapeseed oil methyl esters preparation using heterogeneous catalysts," Bioresource Technology, 1999, pp. 249-253; Elsevier.

Ma et al. "Biodiesel production: a review," Bioresource Technology, 1999, pp. 1-15; Elsevier.

International Search Report and Written Opinion in application No. PCT/US2012/027941 dated Nov. 30, 2012 pp. 1-15.

PCT, "International Search Report and Written Opinion," for international Application No. PCT/US2009/048393, dated Jan. 29, 2010 (15 pgs.).

Suppes et al., "Transesterification of soybean oil with zeolite and metal catalysts," Applied Catalysis A: General, 2004, pp. 213-223, Elsevier.

(56) References Cited

OTHER PUBLICATIONS

Dmytryshyn et al., "Synthesis and characterization of vegetable oil derived esters: evaluation for their diesel additive properties," Bioresouroe Technology, 2004, pp. 55-64, Elsevier.

Vicente et al., "Integrated biodiesel production: a comparison of different homogeneous catalysts systems," Bioresouroe Technology, 2004, pp. 297-305, Elsevier.

Furuta et al., "Biodiesel fuel production with solid superacid catalysis in fixed bed reactor under atmospheric pressure," Catalysis Communications, 2004, pp. 721-723, Elsevier.

Soumanou et al., "Improvement in lipase-cataiyzed synthesis of fatty acid methyl esters form sunflower oil," Enzyme and Microbial Technology, 2003, pp. 97-103, Elsevier.

Khare et al., "Immobilization of Rhizopus Japonicus lipase on celite and its application for enrichment of docosahexaenoic acid in soybean oil," Food Chemistry, 2000, pp. 153-157, Elsevier.

Siler-Marinkovic et al., "Transesterification of sunflower oil in situ," Fuel, vol. 77, No. 12, 1998, pp. 1389-1391, Elsevier.

Schuchardt et al., "Transesterification of Vegetable Oils: a Reivew," J. Braz. Chem. Soc., 1998, pp. 199-210.

Suppes et al., "Calcium Carbonate Catalyzed Alcoholysis of Fats and Oils," JAOCS, 2001, pp. 139-146, AOCS Press.

Darnoko et al., "Kinetics of Palm Oil Transesterification in a Batch Reactor," JAOCS, 2000, pp. 1263-1267, AOCS Press.

Corma et al., "Catalysts for the Production of Fine Chemicals," Journal of Catalysis, vol. 173, 1998, pp. 315-321, Academic Press.

Brat et al., "Fatty Acid Composition of Margarines and Cooking Fats Available on the Czech Market," Journal of Food Composition and Analysis, 2000, pp. 337-343, Academic Press.

Abreu et al., "Utilization of metal complexes as catalysts in the transesterification of Brazilian vegetable oils with different alcohols," Journal of Molecular Catalysis A: Chemical, 2004, pp. 29-33, Elsevier.

Abreu et ai., "New multi-phase catalytic systems based on tin compounds active for vegetable oil transesterificaton reaction," Journal of Molecular Catalyst A: Chemical, 2005, pp. 263-267. Elsevier.

Shimada et al., "Enzymatic aicoholysis for biodiesel fuel production and application of the reaction to oil processing," Journal of Molecular Catalysis B: Enzymatic, 2002, pp. 133-142, Elsevier.

Watanabe et al., "Conversion of degummed soybean oil to biodiesel fuel with immobilized Candida antarctica lipase," Journal of Molecular Catalysis B: Enzymatic, 2002, pp. 151-155, Elsevier.

Barnwal et al., "Prospects of biodiesel production from vegetable oils in India," Renewable & Sustainable Energy Reviews, 2005, pp. 363-378, Elsevier.

Non-Final Office Action re U.S. Appl. No. 13/414,484, dated Jul. 17, 2014.

U.S. Patent and Trademark Office, Office Action re U.S. Appl. No. 11/394,133, dated Dec. 23, 2008.

U.S. Patent and Trademark Office, Office Action re U.S. Appl. No. 11/394,133, dated May 19, 2008.

U.S. Patent and Trademark Office, Office Action re U.S. Appl. No. 11/394,133, dated Sep. 25, 2007.

U.S. Patent and Trademark Office, Office Action re U.S. Appl. No. 11/442,651 dated Apr. 14, 2009.

European Examination Report re Application No. EP 09 770 912.5, dated Jul. 11, 2018.

European Examination report re Application No. 09 770 912.5, dated Mar. 22, 2018.

* cited by examiner

SYSTEM AND METHODS FOR MAKING BIOPRODUCTS

CROSS-REFERENCE TO RELATED APPLICATIONS

This application is a continuation of U.S. patent application Ser. No. 14/518,559, filed Oct. 20, 2014, which is a continuation of U.S. patent application Ser. No. 13/414,484 filed Mar. 7, 2012, which claims the priority benefit of U.S. Provisional Patent Application Ser. No. 61/451,037, filed Mar. 9, 2011; and also claims the priority benefit of U.S. Provisional Patent Application Ser. No. 61/451,040, filed Mar. 9, 2011 and also claims the priority benefit of U.S. Provisional Patent Application Ser. No. 61/451,043, filed Mar. 9, 2011, whose disclosures are incorporated herein by reference in their entirety.

BACKGROUND

Field of the Invention

The present invention relates to a process for making esters. More particularly, it relates to a continuous process for making fatty acid alkyl esters.

Brief Description of Related Art

Biobased products (for example, biodiesel and/or biolubricants) typically include long chain, fatty acid alkyl esters produced from vegetable oils or animal fats by transesterification of the fatty acid glycerides with alcohols. Biodiesel typically include long chain, fatty acid alkyl esters produced from vegetable oils or animal fats by transesterification of the fatty acid glycerides with lower alcohols (for example, methanol and/or ethanol). Biolubricants may be prepared through transesterification of glycerides with alcohols having carbon numbers ranging from 5 to 12 or greater, branched alcohols of similar molecular weight, or transesterification of fatty acid methyl esters. Due to environmental concerns bio-based products in many formulations are being used as substitutes for the petroleum-based products. Biobased products derived from vegetable and plant products, such as soybean, sunflower, and rapeseed etc., are renewable, biodegradable, less environmentally hazardous, and safer to handle. Similarly, other renewable sources of fatty acid glycerides include rendered animal fats and waste cooking oils from commercial food production. Rendered animal fats and waste cooking oils may also be used in the production of biodiesel fuels and biolubricants for automobile applications, mechanical engine applications, cosmetic applications, and soaps.

The heating value of vegetable oil is similar to that of fossil fuel (for example, diesel), but the direct use of vegetable oils in the diesel engines is limited by some of their physical properties. For example, the viscosity of vegetable oil is about 10 times the viscosity of diesel fuel.

Transesterification of fatty acid glycerides may be used to improve the fuel value and lubricant utility of the fatty acid glycerides. The production of useful industrial compounds from naturally-derived and sustainably-produced fatty acid glycerides is made difficult by the presence of lipophilic or oil soluble material which must be removed to permit the following transesterification to reach a high level of conversion and economic efficiency. Such problems with seed oils include degumming, the removal of phospholipids; deodorizing, the removal of free fatty acids; and bleaching, the removal of finely divided solids and colored materials. Conventional processes that use alkaline catalysts for the production of fatty acid methyl esters may be highly sensitive to the presence of contaminates in the fatty acid glyceride phase.

Moisture may deactivate the alkaline catalyst. Free fatty acids present in the starting material may inactivate the alkaline catalyst and produce soaps; and unsaponifiable materials may react with such catalysts. Water and/or soaps interfere with the separation of glycerin from the fatty acid alkyl ester mixtures. Additionally, the final product may have to be blended with other oils to adjust the free fatty acid content and/or reduce the content of contaminants in the final product.

Conventional means for recovering valuable glycerin from naturally-derived and sustainably-produced fatty acid glycerides involves saponification of the fatty acid glyceride which affords a crude glycerin product in an aqueous mixture. The crude mixture may or may not include salts and other undesirable materials, requiring expensive dewatering and further refinement.

Processes for the transesterification of fatty alkyl esters using heterogeneous catalysts have been developed. Many of the processes require separation of the catalyst from the system and/or further processing to remove glycerin and/or other by-products of the transesterification process.

U.S. Pat. No. 7,754,643 to Srinivas et al., which is incorporated herein by reference, describes a catalyst and method of use for the transesterification of glycerides, fatty acid esters and cyclic carbonates.

U.S. Pat. No. 7,482,480 to Srinivas et al., which is incorporated herein by reference, describes a process for the preparation of hydrocarbon fuel that includes contacting fatty acid glycerides with alcohols in the presence of a solid, double metal cyanide catalyst at a temperature in the range of 150° to 200° C. for a period of 2-6 hrs and separating the catalyst from the above said reaction mixture to obtain the desired hydrocarbon fuel.

U.S. Pat. No. 7,842,653 to Darbha et al. describes a batch process for the preparation of lubricants from vegetable oil or fat obtained from animal source that involves a reaction of vegetable oil or fat with an alcohol in the presence of a double metal cyanide catalyst, at a temperature in the range of 150° to 200° C. for a period of 3 to 6 hrs to obtain the desired biolubricant.

International Application Publication No. WO/2009/113079 to Srinivas et al., which is incorporated herein by reference, describes a process for the preparation of biofuels or biofuel additives from glycerol.

U.S. Pat. No. 8,124,801 to Srinivas et al., which is incorporated herein by reference, describes a batch process for the preparation of fatty acid alkyl esters using a catalyst that includes a metal from Group VIB of the Periodic Table, a metal from Group IIIA of the Periodic Table and an element group VA of the Periodic Table.

U.S. Patent Application Publication no. 2010/0108523 to Sams et al., which is incorporated herein by reference, describes removal of glycerin from biodiesel using an electrostatic process.

U.S. Pat. No. 7,531,688 to Fleischer, which is incorporated herein by reference, a method for making fatty acid alkyl esters by reacting fatty acid glycerides with an excess of alcohol in a pressurized environment, where the unreacted alcohol component is separated from the reaction product by a flash purification techniques.

Conventional processing (for example, batch processing) to prepare fatty acid alkyl esters, removal of excess alcohols and other volatile compounds is done by reducing a pressure of the reaction vessel and distilling or flashing the excess alcohol from the reaction vessel until all or substantially all of the alcohol is removed from the reaction vessel, which may cause prolonged heating of the reaction mixture in the presence of the alcohol. Prolonged heating of the reaction product may cause thermal degradation of the fatty acid alkyl esters and/or hydrolysis of the fatty acid alkyl esters. Thus, an efficient method of removing alcohols and/or water from the reaction mixture is highly desired.

As described, many methods and/or catalysts for the transesterification of fatty alkyl acids have been proposed, however, many methods require purification of starting materials, removal of water from the starting fatty alkyl acid, and/or steps to remove by-products formed from the esterification reactions. Hence, an efficient method of transesterifying both edible and non-edible vegetable oils in refined or unrefined forms at mild conditions is highly desirable. Moreover, an efficient method of simultaneously converting free fatty acid contaminants of naturally-derived and sustainably-produced fatty acid glycerides at mild conditions is highly desirable. Such combined methods enable economic benefits and make the bioproducts an economical alternative to petroleum based diesel and lubricants.

SUMMARY

Embodiments described herein describe systems and methods for producing fatty acid alkyl esters.

In some embodiments, a method of continuously making fatty acid alkyl esters includes determining a flow rate of a feedstock stream, wherein the feedstock stream comprises one or more fatty acid glycerides; contacting the feedstock stream and an alcohol stream with a heterogeneous acidic catalyst to produce a reaction mixture stream having a predetermined flow rate from the reactor, wherein the reaction mixture stream comprises unreacted alcohol, one or more fatty acid alkyl esters, and glycerin; and separating substantial portion of the unreacted alcohol while cooling a portion of the reaction mixture.

In some embodiments, a system of continuous manufacture of fatty acid alkyl esters includes at least one mixing device for mixing one or more alcohol compounds and one or more feedstocks, wherein the feedstock comprises one or more fatty acid glycerides and one or more free fatty acids; a reactor, the reactor being capable of receiving a flow from the mixing device, wherein, during use, allows contact of the flow with a heterogeneous acidic catalyst; a device coupled to the reactor, wherein the device receives flow from the reactor and allows a sudden drop in pressure to induce removal of one or more volatile compounds from the reaction mixture exiting the reactor while maintaining a desired pressure of the reactor, wherein the reaction mixture comprises one or more of the alcohol compounds, one or more fatty acid alkyl esters, glycerin, or mixtures thereof; and a separator coupled to the device, the separator capable of receiving flow from the device, separating at least one alcohol compound from the reaction mixture, and cooling a portion of the reaction mixture.

In some embodiments, a system of continuous manufacture of fatty acid alkyl esters includes at least one mixing device for mixing one or more alcohol compounds and one or more feedstocks, a reactor, the reactor being capable of receiving a flow from the mixing device, at least one analyzer coupled to the reactor, a device coupled to the reactor; and a separator coupled to the device, the separator capable of separating the glycerin from the one or more fatty acid alkyl esters using an electrostatic field. The analyzer measures concentrations of the reaction mixture in the reactor. The device allows a sudden drop in pressure to induce removal of one or more of the alcohol compounds and/or water from the reaction mixture.

In some embodiments, a method of continuous manufacture of fatty acid alkyl esters includes, assessing a total amount of fatty acid glycerides and/or a total amount of alcohol in a fatty acid glyceride/alcohol feedstock stream, determining a flow rate of the fatty acid glyceride/alcohol feedstock stream; contacting at least a portion of the fatty acid glyceride/alcohol feedstock stream with one or more catalysts, obtaining an analysis of a reaction mixture formed from contact of the fatty acid glyceride/alcohol feedstock stream with at least one of the catalysts, assessing a concentration of at least the fatty acid glycerides, at least one of the fatty acid alkyl esters, or glycerin from at least one of the obtained analyses, and adjusting one or more contacting conditions based on at least one of the assessed concentrations. The flow rate of the feedstock stream may be based on the assessed amount of fatty acid glycerides and/or assessed amount of alcohol in the fatty acid glyceride/alcohol feedstock stream.

In some embodiments, a method of making one or more bioproducts using quality control includes collecting data from one or more continuous processes to produce one or more bioproducts, wherein the data set includes a) conversion data for one or more feedstocks to fatty acid methyl esters, b) catalyst aging, c) feedstock selection, d) reaction product composition, e) by-product composition, f) quality of at least one of the bioproducts, or g) combinations thereof, wherein the at least one of the feedstocks comprise one or more fatty acid glycerides and/or one or more alcohol; and adjusting one or more parameters of the continuous process based on the collected data to maintain or adjust a quality of at least one of the bioproducts produced.

In some embodiments, a method of making bioproducts, includes determining a flow rate of a feedstock stream, contacting the feedstock stream and an alcohol stream with a heterogeneous acidic catalyst to produce a reaction mixture stream having a predetermined flow rate, and adjusting a temperature and a pressure of the reaction mixture stream such that an alcohol stream separates from the reaction mixture at a rate sufficient to remove a majority of the alcohol and water while inhibiting hydrolysis of the fatty acid alkyl ester products.

In some embodiments, a method of making one or more bioproducts, includes determining a flow rate of a feedstock stream having a water content of greater than 2 percent by weight, contacting at least a portion of the wet feedstock with a catalyst in the presence of one or more alcohols to produce a reaction mixture, separating a fatty acid alkyl esters/glycerin stream from the reaction mixture, and applying an electrostatic field to fatty acid alkyl esters/glycerin stream such that an fatty acid alkyl esters stream separates from the fatty acid alkyl esters/glycerin stream. The fatty acid alkyl esters/glycerin stream having a water content of at most 2 percent by weight.

In some embodiments, a method of making one or more bioproducts includes assessing an amount of free fatty acids in a feedstock stream, determining a flow rate of the feedstock stream, determining a flow rate of an alcohol stream, contacting at least a portion of the feedstock stream and the alcohol stream with a heterogeneous acidic catalyst to produce a reaction mixture stream; and separating a fatty acid alkyl esters stream from the reaction mixture stream. The flow rate of the alcohol stream may be determined based on a predetermined mole ratio of alcohol to free fatty acid.

In some embodiments, a method of making one or more bioproducts, includes determining a flow rate of a feedstock stream that includes one or more fatty acid glycerides; determining a flow rate of an alcohol stream comprising one or more alcohols, contacting at least a portion of the feedstock stream with a heterogeneous acidic catalyst in the presence of the alcohol stream to produce a reaction mixture stream, and separating a fatty acid alkyl esters stream from the reaction mixture stream. The flow rate of the alcohol stream may be determined based on a predetermined mass ratio of total alcohols to total fatty acid glycerides in the feedstock stream.

In some embodiments, a method of making biodiesel and biolubricants, includes contacting at least a portion of a feedstock with a heterogeneous acidic catalyst to produce a first mixture, separating a fatty acid methyl ester/glycerin stream from the reaction mixture, applying an electrostatic field to the fatty acid methyl ester/glycerin stream such that an fatty acid methyl ester stream separates from the fatty acid methyl ester/glycerin stream, contacting the fatty acid methyl ester stream with an additional heterogeneous acidic catalyst in the presence of a stream that includes one or more alcohols or polyols to produce a second mixture, and separating one or more fatty acid alkyl esters from the second mixture. At least one of the alcohols or polyols has a carbon number greater than 5 and at least one of the fatty acid alkyl esters includes an alkyl group having a carbon number of at least 5.

In some embodiments, a method of making omega 3 and omega 6 fatty acids includes contacting a feedstock rich in polyunsaturated fatty acids with a heterogeneous acidic catalyst in the presence of one or more alcohols to produce a reaction mixture, and separating at least one or more of the polyunsaturated fatty acids from the reaction mixture. The one or more polyunsaturated fatty acids may include an omega 3 and/or an omega 6 fatty acid.

In some embodiments, the feedstock includes one or more fatty acid glycerides, one or more free fatty acids, a stream that includes methanol and a stream that includes fatty acid glycerides, or combinations thereof. The fatty acid glycerides stream may contain at least 20 percent by weight free fatty acids. In some embodiments, the feedstock includes one or more fatty acid glycerides and a predetermined amount of one or more polyunsaturated fatty acids. In some embodiments, at least one of the catalysts may include an acidic heterogeneous catalyst. In some embodiments, the reaction mixture may include one or more compounds of the feedstock unreacted fatty acid glycerides, one or more fatty acid alkyl esters, glycerin, unreacted alcohols, or mixtures thereof.

In further embodiments, features from specific embodiments may be combined with features from other embodiments. For example, features from one embodiment may be combined with features from any of the other embodiments. In further embodiments, bioproducts are produced using any of the methods and/or systems described herein. In further embodiments, additional features may be added to the specific embodiments described herein.

DETAILED DESCRIPTION

Figure 1:
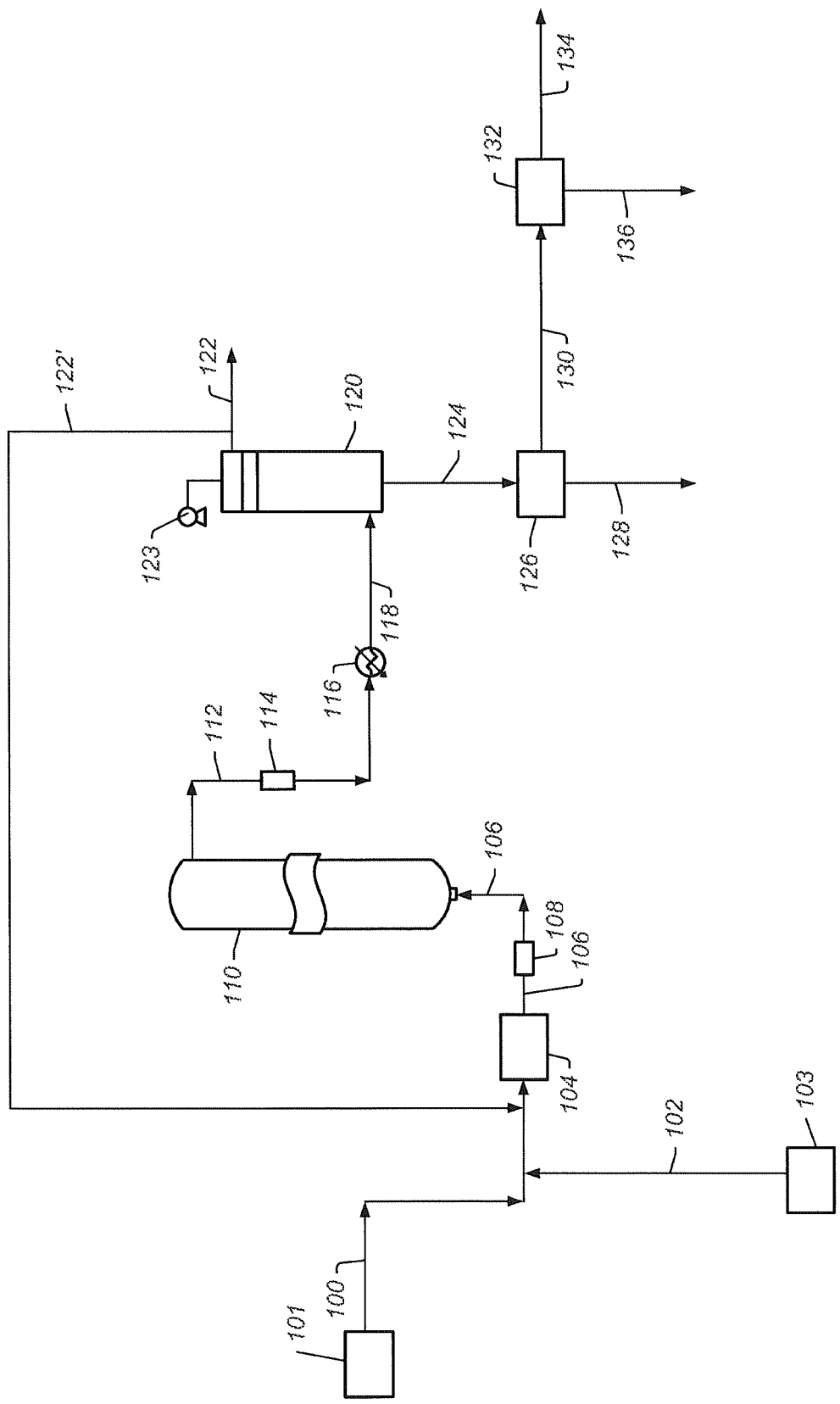
FIG. 1 illustrates one exemplary embodiment of a continuous process for producing fatty acid alkyl esters.

Embodiments of methods described herein provide an efficient process for manufacturing of fatty acid alkyl esters in high yields at mild conditions. Such a fatty acid alkyl ester may be used as a biofuel, for example, biodiesel, or used as a biolubricant. In some embodiments, the method is a continuous process for the production of biodiesel and biolubricants from fatty acid glycerides containing significant amount of free fatty acids and/or water. The process is atom-efficient and moderate reaction conditions (for example, temperature and pressure) are employed. Unlike conventional methods, the methods described herein are more efficient even with non-edible oil containing free fatty acids and water impurity in oil. Thus, there are few to no limitations on the quality of oil that may be used.

Minimally refined naturally occurring or sustainably-produced fatty acid glycerides may be converted into fatty acid alkyl ester mixtures with high efficiency. Such minimal processing may include among other inexpensive processes such as the filtration of insoluble materials or decantation of gross amounts of water. Further, unlike conventional alkaline or other solid acid catalyzed processes, free fatty acids are converted into alkyl fatty acid esters with high efficiency and fatty acid glycerides are also converted into alkyl fatty acid esters, also in high efficiency in one step.

Utilizing a continuous process to produce alkyl fatty acid esters allows automation to be incorporated into overall process. Automation may be used to regulate quantities and perform assays on a continuous basis, thus better production economics and greater asset utilization are realized. Using a continuous process improves product consistencies as compared to a batch process, thus, quantities of high quality products are produced.

In some embodiments, a continuous process may include use of one or more analyzers to determine quantities and/or qualities of fatty acid glyceride feedstocks and/or alcohol streams used in the continuous process. Examples of analyzers include, but are not limited to, near infrared spectrometers, liquid chromatographs, gas chromatographs, mass spectrometers, nuclear magnetic resonance spectrometers or combinations thereof. In some embodiments, one or more analyzers are coupled to one or more units of the continuous process. The analyzer may be an infrared fiber-optic probe or a flow cell coupled to one or more units.

Continuous flow through a reactor allows for "real time" reaction monitoring of the reaction mixture, thus reaction times may be minimized. Monitoring the reaction allows for adjustment of reaction conditions such that by-products of the transesterification reaction are minimized. Reaction conditions include, but are not limited to, flow rate, temperature, pressure, mass ratios (alcohol to feedstock) or combinations thereof. Monitoring of the reaction mixture may include assessing the amount of product produced, assessing the amount of one or more starting materials, and/or assessing an amount of by-products in the reaction mixture. For example, the appearance of product peaks and/or the absence of starting material may be monitored. The reaction may be monitored using spectrometry techniques (for example, near infrared, nuclear magnetic resonance), chromatographic techniques (for example, gas chromatography and/or liquid chromatography). In some embodiments, near infrared spectrometry is used to monitor the progress of the reaction in reactor 110.

Monitoring may be performed using off-line and/or in-line analyses. "Off-line analysis" refers obtaining an analysis using an instrument not directly coupled to the system. For example, a sample may be obtained at the inlet of a reactor and analyzed using an instrument at a location away from the reactor. "In-line sampling" refers to obtaining an analysis using an instrument and/or other analysis instrumentation directly coupled to the continuous system. For example, a near infrared spectrometer may be coupled to a reactor and/or one or more conduits of the system.

Obtaining an analysis may include development of calibration curves. For example, calibration curves may be established for water content in methanol and/or the fatty acid glyceride feedstock, unsaponifiable materials in the glyceride feedstock, and products in a reaction mixture. Comparison of reagents and/or reaction products to the calibration curves enhances product consistency and production of higher quality materials as compared to batch processing.

In some embodiments, the quality of the reagents and/or starting materials is assessed. For example, water content and content of compounds that are unsaponifiable (for example, compounds that cannot be converted to soaps) of the fatty acid glyceride feedstock. Methanol may be assayed (for example, assayed using near infrared spectrometry) to determine the amount of water in the methanol. In some embodiments, the fatty acid glyceride feedstock/alcohol stream is monitored (for example, using near infrared analysis) to determine the mass ratio of the fatty acid glyceride feedstock to the alcohol. Based on the determined mass ratio, an amount of alcohol and/or fatty acid glyceride feedstock may be adjusted to meet a pre-determined mole ratio. In some embodiments, a flow rate of the fatty acid glyceride feedstock stream, the alcohol stream and/or the fatty acid glyceride feedstock/alcohol stream is determined based on the assessed amount of fatty acid glycerides, assessed amount of alcohol, and/or assessed amount of free fatty acids in the feed streams and/or the reaction product streams.

In some embodiments, a continuous manufacture of bioproducts (for example, fatty acid alkyl esters), assessing a total amount of fatty acid glycerides and/or a total amount of alcohol in a feedstock stream. The feedstock stream may include fatty acid glycerides and alcohol compounds. The flow rate of the feedstock stream may be determined based on the assessed amount of fatty acid glycerides and/or alcohol in the feedstock stream. In some embodiments, a flow rate of the feedstock stream may be based on a predetermined mole ratio of alcohol to free fatty acid. In certain embodiments, a flow rate of the feedstock stream may be based on a predetermined mass ratio of alcohol to fatty acid glyceride. The feedstock stream may be contacted with and/or flowed over one or more acidic heterogeneous catalysts. An analysis of a reaction mixture stream formed from contact of the feedstock with at least one of the catalysts may be obtained after a period of time. The reaction mixture stream may include fatty acid glycerides, one or more fatty acid alkyl esters, glycerin, unreacted alcohols, or mixtures thereof. A concentration of at least the fatty acid glycerides, at least one of the fatty acid alkyl esters, or glycerin from may be assessed from at least one of the obtained analysis. One or more contacting conditions may be adjusted based on at least one of the assessed concentrations.

In addition, the continuous process described herein uses no water and produces very little in the way of waste products, and worker exposure to regulated materials (for example, methanol) is limited. In comparison, conventional processing requires measuring and handling sodium methoxide or sodium or potassium hydroxide and then, either hydrochloric acid or sulfuric acid for neutralization of catalyst. This leads to extensive water use to remove salts, soaps or other post-processing steps, which while eliminating direct use of water defers the water consumption to resin regeneration or other step to reuse the "dry wash" agent.

In a batch process or a continuous process using alkaline catalyst rapid distillation of alcohols (for example, methanol) from a reaction mixture containing residual catalyst, fatty acid alkyl esters, methanol, water is difficult due to the partitioning of the alcohol between the alcohol/water phase and the fatty acid alkyl ester/glycerin phases. Furthermore, use of an alkaline catalyst may allow soaps to form in the reaction mixture that, under reduced pressure distillation and/or flash distillation, cause foaming in the reaction mixture. Creation of foam may entrain reaction products (for example, fatty acid alkyl esters) in the alcohol and cause loss of product. Multiple distillation and/or separation steps may be required to remove catalyst, alcohol, glycerin and/or to obtain fatty acid alkyl esters suitable for commercial use.

Use of an acidic heterogeneous catalyst in a batch process requires separation of the catalyst from the reaction mixture upon completion of the process to obtain fatty acid alkyl esters suitable for commercial use and to recycle the catalyst. Separation of catalyst from the reaction mixture requires extra equipment and increased processing time, as well as additional equipment to recover and recycle the catalyst. Failure to recycle can lead to higher cost of production. Residual catalyst remaining in the reaction mixture may promote hydrolysis of the fatty acid alkyl ester to fatty acids and alcohol, thus the purity of the product may be affected.

Using continuous separation (for example, flash distillation) of alcohols, water and/or other volatile components from the reaction mixture in fully continuous process allows for removal of methanol and/or water from the reaction mixture such that hydrolysis of the fatty acid alkyl esters and/or thermal degradation of the fatty acid alkyl ester is inhibited or significantly reduced as compared to batch processing of the reaction mixture. Furthermore, use of a continuous process does not require separation of the catalyst from the reaction mixture prior to the removal of methanol, as the catalyst remains in the reactor 110 in a fixed bed or other suitable configuration.

In the some embodiments, using a continuous process allows recovery of glycerin in an essentially anhydrous, highly pure liquid state and containing no salts. The separated alkyl fatty acids ester mixtures are recovered as distilled liquids containing no or substantially no high boiling partially converted glycerides. The absence of high boiling partially converted glycerides makes the alkyl fatty acid ester mixture suitable for use as fuel without further purification as high boiling partially converted glycerides are detrimental to fuels, causing problems such as plugged fuel lines, blocked injectors and poor combustion.

In some embodiments, bioproducts are produced through esterification of fatty acids with alcohols. The esterification is performed at moderate conditions and shorter reaction times as compared to batch processing and/or other conventional processes. Biodiesel may be produced through esterification of fatty acids with alcohols having carbon numbers ranging from 1 to 4 ($C_1$ to $C_4$). Biolubricants may be produced by transesterification of fatty acid alkyl esters or esterification of fatty acids with alcohols or polyols having a carbon number ranging from $C_5$ to $C_{12}$ or branched alcohols of similar molecular weight. In some embodiments, bioproducts are produced by esterification of fatty acid glycerides with of one or more alcohols using a heterogeneous acidic catalyst. As used herein, "heterogeneous catalyst" refers to a catalyst that is in a different phase (for example, a solid catalyst described herein) to other compounds (for example, liquid or vapor) when mixed together. The catalyst may be separated easily by removal from a fixed bed reactor or separated from a mixture by centrifugation or by simple filtration and re-used.

In an embodiment, fatty acid glyceride feedstocks may be low quality oils. The ability to use low quality as well as high quality fatty acid glycerides (for example, natural animal or plant oils) allows bioproducts to be produced in areas where natural plant oils are not abundant. Fatty acid glyceride feedstocks include, but are not limited to, fatty acid monoglycerides, fatty acid diglycerides and fatty acid triglycerides obtained from raw, unrefined and partially-refined oils (for example, oils from plants and/or plant seeds), inedible and non-food oils, algal oils, animal fats, waste cooking oils and mixtures thereof. Examples of fatty acid glyceride feedstocks include glycerides derived from fatty acids and/or oils that include fatty acid glycerides and free fatty acids. Examples of oils that may be used as fatty acid glyceride feedstocks include, but are not limited to, oils from plant seeds, *camellia* oil, coconut oil, palm oil, pennycress oil, meadowfoam (Limnanthes alba) oil, sunflower oil, soybean oil mustard oil, olive oil, cotton seed oil, rapeseed oil, margarine oil, jojoba oil, Jatropha oil, karanja oil, vegetable oil, animal fat, grease, waste cooking oil, or mixtures thereof. In some embodiments, a content of triglycerides in a fatty acid glyceride feedstock may range from 10% to 99.9% by weight, from about 30% to about 95% by weight, or from about 50% to about 90% by weight.

In some embodiments, the fatty acid glyceride feedstock may include from 5 percent up to 100 percent, 10 percent to 80 percent, 15 percent to 60 percent by weight or 20-50 percent by weight free fatty acids. The term "free fatty acid" generally refers to a long chain carboxylic acid with a long hydrocarbon chain (for example, a carbon number greater than 6). Examples of free fatty acids include, but are not limited to, saturated fatty acids, unsaturated fatty acids and polyunsaturated fatty acids.

Examples of saturated fatty acids include, but are not limited to: hexanoic acid (caproic acid); octanoic acid (caprylic acid); decanoic acid (capric acid); dodecanoic acid (lauric acid); tridecanoic acid; tetradecanoic acid (myristic acid); pentadecanoic acid; hexadecanoic acid (palmitic acid); heptadecanoic acid (margaric acid); octadecanoic acid (stearic acid); eicosanoic acid (arachidic acid); docosanoic acid (behenic acid); tricosanoic acid; and tetracosanoic acid (lignoceric acid).

Examples of monounsaturated fatty acids include, but are not limited to: 9-tetradecenoic acid (myristoleic acid); 9-hexadecenoic acid (palmitoleic acid); 11-octadecenoic acid (vaccenic acid); 9-octadecenoic acid (oleic acid); 11-eicosenoic acid; 13-docosenoic acid (erucic acid); 15-tetracosanoic acid (nervonic acid); 9-trans-hexadecenoic acid (palmitelaidic acid); 9-trans-octadecenoic acid (elaidic acid); 8-eicosaenoic acid; and 5-eicosaenoic acid.

Examples of polyunsaturated fatty acids include, but are not limited to omega-3 polyunsaturated fatty acids, omega-6 polyunsaturated fatty acids; and conjugated polyunsaturated fatty acids. Examples of omega-3 polyunsaturated fatty acids include, but are not limited to: 9,12,15-octadecatrienoic acid (alpha-linolenic acid); 6,9,12,15-octadecatetraenoic acid (stearidonic acid); 11,14,17-eicosatrienoic acid (eicosatrienoic acid (ETA)); 8,11,14,17-eicsoatetraenoic acid (eicsoatetraenoic acid); 5,8,11,14,17-eicosapentaenoic acid (eicosapentaenoic acid (EPA)); 7,10,13,16,19-docosapentaenoic acid (docosapentaenoic acid (DPA)); 4,7,10,13,16,19-docosahexaenoic acid (docosahexaenoic acid (DHA)); 6,9,12,15,18,21-tetracosahexaenoic acid (nisinic acid); 9E,11Z,15E-octadeca-9,11,15-trienoic acid (rumelenic acid); 9Z,11E,13E,15Z-octadeca-9,11,13,15-trienoic acid (α-parinaric acid); and all trans-octadeca-9,11,13,15-trienoic acid (β-parinaric acid). Examples of omega-6 polyunsaturated fatty acids include, but are not limited to: 9,12-octadecadienoic acid (linoleic acid); 6,9,12-octadecatrienoic acid (gamma-linolenic acid); 11,14-eicosadienoic acid (eicosadienoic acid); 8,11,14-eicosatrienoic acid (homo-gamma-linolenic acid); 5,8,11,14-eicosatetraenoic acid (arachidonic acid); 13,16-docosadienoic acid (docosadienoic acid); 7,10,13,16-docosatetraenoic acid (adrenic acid); 4,7,10,13,16-docosapentaenoic acid (docosapentaenoic acid); 8E,10E,12Z-octadecatrienoic acid (calendic acid); 9Z,11E-octadeca-9,11-dienoic; 8E,10E,12Z-octadecatrienoic acid (a-calendic acid); 8E,10E,12E-octadecatrienoic acid (β-calendic acid); 8E,10Z,12E-octadecatrienoic acid (jacaric acid); and 5Z,8Z,10E,12E,14Z-eicosanoic acid (bosseopentaenoic acid). Examples of conjugated polyunsaturated fatty acids include, but are not limited to: 9Z,11E-octadeca-9,11-dienoic acid (rumenic acid); 10E,12Z-octadeca-9,11-dienoic acid; 8E,10E,12Z-octadecatrienoic acid (α-calendic acid); 8E, 10E,12E-octadecatrienoic acid (β-calendic acid); 8E,10Z,12E-octadecatrienoic acid (jacaric acid); 9E,11E,13Z-octadeca-9,11,13-trienoic acid (a-eleostearic acid); 9E,11E,13E-octadeca-9,11,13-trienoic acid (β-eleostearic acid); 9Z,11Z,13E-octadeca-9,11,13-trienoic acid (catalpic acid); 9E,11Z,13E-octadeca-9,11,13-trienoic acid (punicic acid); 9E,11Z,15E-octadeca-9,11,15-trienoic acid (rumelenic acid); 9E,11Z, 13Z,15E-octadeca-9,11,13,15-trienoic acid (α-parinaric acid); all trans-octadeca-9,11,13,15-trienoic acid (β-parinaric acid); and 5Z,8Z,10E,12E,14Z-eicosapentanoic acid (bosseopentaenoic acid).

A content of free fatty acid in the feedstock may be determined using standardized test methods (for example, ASTM Test Method D1585 or D664). In some embodiments, the fatty acid glyceride feedstock may include at least 5 percent, at least 10 percent or at least 20 percent of animal fat (for example, beef tallow). In some embodiments, the fatty acid glyceride feedstock includes from about 20 percent to about 90 percent, from about 30 percent to about 80 percent, or from about 40 percent to 70 percent free fatty acids. In one embodiment, the fatty acid glyceride contains at least 90 percent free fatty acid. In some embodiments, substantially all of the free fatty acids and fatty acid glycerides in the feedstock are converted to fatty acid alkyl esters in one step. Thus, the fatty acid content in fatty acid alkyl ester product does not need to be adjusted prior to selling the fatty acid alkyl ester product. Use of feedstocks having free fatty acids eliminates the need to pretreat the feedstock to remove free fatty acids for separate processing or to be sequentially processed to convert first free fatty acid to esters, followed by converting the fatty acid alky ester-fatty acid glyceride mixture to solely fatty acid alkyl esters. The ability to use feedstocks containing free fatty acids is a savings in both capital and operating cost.

The fatty acid glyceride feedstock may contain a significant amount of water from prior processing. For example, the fatty acid glyceride feedstock may contain at least 1 percent by weight of water. In some embodiments, a fatty acid glyceride feedstock may have a water content ranging from 1 to about 30 percent by weight, from about 2 to about 20 percent by weight, or from 3 to about 5 percent by weight. Fatty acid glyceride feedstocks containing high amounts of water may separated into a water phase and an oil phase. The water phase may be removed prior to processing the fatty acid glycerides feedstock. In some embodiments, removal of separated water is not necessary.

Alcohols used in the transesterification of the fatty acid glyceride feedstock may have from 1 to 50, from 2 to 25, or from 3 to 12 carbon atoms. Alcohols include hydrocarbons having at least one hydroxy group. Examples of alcohols include primary alcohols, diols, triols and polyols. In some embodiments, the alcohols are primary alcohols. Alcohols include, but are not limited to, methanol, ethanol, propanol, butanol, pentanol, octanol, 2-ethylhexanol, decanol, dodecanol, glycerin, glycols (for example, propylene glycol 1,2 and propylene glycol 1,3,) neopentyl glycol, trimethylol propane, pentaerythritol or mixtures thereof.

In some embodiments, a molar ratio of total fatty acid glycerides to alcohol may range from about 1:6 to 1:50, from 1:10 to 1:40, or from 1:20 to 1:30. In some embodiments, molar ratio of total fatty acid glycerides to methanol is greater than 1:12, for example a molar ratio of total fatty acid glyceride to methanol is 1:15. In an embodiment, a mass ratio of methanol to total fatty acid glyceride ranges from about 0.40 to about 1, from about 0.5 to about 0.9 or from about 0.5 to 0.8. As used herein, "total fatty acid glycerides" includes all glyceride functionality determined from all glycerides in the feedstock (for example, monoglycerides, diglycerides, and triglycerides).

In some embodiments, molar ratio of total free fatty acid to alcohol may range from about 1:6 to 1:50, from 1:10 to 1:40, or from 1:20 to 1:30. In some embodiments, molar ratio of total free fatty acid to methanol is greater than 1:12, for example a molar ratio of total free fatty acids to methanol is 1:15. In an embodiment, a mass ratio of methanol to total free fatty acids ranges from about 0.40 to about 1, from about 0.5 to about 0.9 or from about 0.5 to 0.8.

In certain embodiments, alcohols having 1 to 4 carbon atoms are reacted with a fatty acid glyceride feedstock to form fatty acid alkyl esters suitable for use as a biodiesel fuel. Biolubricants may be made by reaction of alcohols having 5 to 50 carbon atoms with the fatty acid glyceride or fatty acid alkyl ester feedstock. In an embodiment, the fatty acid alkyl ester made using the process described herein has 15 to 70 carbon atoms is used as a biolubricant. In some embodiments, the mole percent conversion of fatty acid glycerides is 90 to 100 mol % and the biodiesel/biolubricant selectivity is greater than 95%. Examples, of fatty acid alkyl esters made by the process described herein include, but are not limited to, alkyl esters of myristic, palmitic, palmitoleic, stearic, oleic, linoleic, linolenic, arachidic acids, or mixtures thereof.

The processes described herein may use a catalyst that has the added advantages of low cost and more run time life. In some embodiments, the catalyst is solid. In certain embodiments, the catalyst has acidic properties. Examples of the catalyst having acidic properties and preparation thereof are found in U.S. Pat. No. 8,124,801 to Srinivas et al.

In certain embodiments, catalyst includes one or more metals from Group VIB of the Periodic Table. The Group VIB metals may be inorganic salts (for example, nitrates, sulfates), and/or oxides. In some embodiments, the Group VIB metal is molybdenum or molybdenum oxide. An amount of Group VIB metal, calculated as metal by weight of catalyst, may range from about 0.01% to about 10%, from about 0.5% to 5%, or from 1% 5% Group VIB metal by weight of catalyst. An amount of Group VIB metal oxide may range from about 5% to about 20%, from about 8% to about 17%, or from about 10% to about 15% Group VIB metal oxide by weight of catalyst.

In some embodiments, the catalyst includes one or more metals from Group VIB of the Periodic Table described herein and a promoter. The promoter may be one of more elements from Group VA of the Periodic Table, for example, phosphorus or phosphorus compounds. In certain embodiments, the Group VA element (promoter) is a phosphorus compound. In an embodiment, the Group VA element is present in the range of about 0.1% to about 7%, about 0.5% to about 5%, about 1% to about 3% by weight of the catalyst.

In some embodiments, the catalyst includes one or more metals from Group VIB of the Periodic Table described herein, a co-promoter and/or a promoter. The co-promoter may include metals or compounds of metals from Group IA of the Periodic Table, Group IIA of the Periodic Table, Group IIIB of the Periodic Table, Group VIII of the Periodic Table, or mixtures thereof. Examples of metals from Group IA, Group IIA, Group IIIB, or Group VIII of the Periodic Table include, but are not limited to, sodium, potassium, calcium, lanthanum, and nickel. An amount of co-promoter in the catalyst may range from about 0.0001% to about 10%, about 0.005% to about 8% or 0.5% to about 5% by weight of catalyst. In some embodiments, the catalyst may contain from about 0.05% to about 6.5% calcium by weight of the catalyst. In some embodiments, the catalyst may include from 0.0001% to about 7.8% sodium and/or potassium by weight of the catalyst. In some embodiments, the catalyst may include from about 0.0001% to about 4.5% lanthanum by weight of catalyst. In some embodiments, the catalyst may include from 0.0001% to about 5.5% nickel by weight of catalyst.

The Group VIB metals, Group VIB metal compounds, promoters, co-promoters, or mixtures thereof may be supported on one or more oxides of one or more metals from Group IVB of the Periodic Table. Examples of Group IVB metal oxides (refractory oxides) include, but are not limited to, alumina oxide and/or titanium oxide. The refractory inorganic oxide may be of synthetic or natural origin and have a medium to a high surface area, and a well-developed pore structure. In an embodiment, hydrated alumina, when used as a support material, results in a product where the morphology of the active materials is well maintained in the resulting catalyst composition.

The catalytic metals (for example, Group VIB metals) may be applied to a formed or unformed support by one of several methods known in the art. This is usually followed by forming, if necessary, and by calcinations to convert the catalytic metal compounds to oxides. U.S. Pat. No. 3,287,280 to Colgan et al. and U.S. Pat. No. 4,048,115 to O'Hara, both of which are incorporated herein by reference describe methods for the preparation of supported catalysts.

The intermediate support material of the catalyst may be prepared by either a solid mixing method or by a solution addition and subsequent mixing method. In both cases, the precursor of the support material (for example, alumina oxide) is well peptized with suitable mineral acid, for example, nitric acid and acetic acid. In an embodiment, nitric acid in the range of 1.0-10.0% of the support mass is used for peptization. The support precursor may be any of the Group IIIA or IVA refractory metal oxides or their combinations. In an embodiment, the Group IIIA metal oxide is alumina. In certain embodiments, a Group IIIA metal oxide is peptized with a mineral acid in the range of about 1% to about 10% or about 2% to 8%, or about 3% to about 7% by weight of the support material. For example, alumina oxide is peptized with nitric acid. In an embodiment, blending of various precursors of these metal oxides is performed to obtain suitable pore size distribution.

After peptization, active catalytic compounds, for example, metal oxides precursors of Group VIB, may be added along with the promoter selected from Group VA of the Periodic Table and/or co-promoter. In some embodiments, the co-promoter is added prior to forming the catalyst (for example, during extrusion), but before drying and/or calcination of the catalyst. The composition of the active metal, for example, molybdenum, may be incorporated using impregnation, compounding, extruding trials, various combinations of the processes described herein, or methods known in the art. A proper selection of appropriate preparation conditions may be made using methods known in the art. In some embodiments, the active metal precursor, the promoter precursor, and/or co-promoter may be added either as separate compounds or together as slurry. For example, the metal precursor and the promoter precursor may be combined by mixing two aqueous solutions together. An appropriate morphology and texture of the metal components may be achieved by applying suitable methods and combination of precursors. In an embodiment, the size and shape of the supported systems were to optimize, for example, tuning geometrical surface area. The surface area of the catalyst may range from 50 $m^2/g$ to 300 $m^2/g$.

The catalyst may have a pore volume ranging from 0.2 ml/g to 0.95 ml/g, or from 0.5 ml/g to 0.7 ml/g. Pore volume of samples may be determined by filling the pore space to saturation by applying water. The quantity of water is determined by its volume added or the weight increase of the sample. The pore space can be filled by putting the quantitatively known sample in excess water and the excess water is removed, and the saturated catalyst samples were weighed again to determine the total water uptake.

In some embodiments, the catalyst composition resulting from the above described process may be directly shaped. Shaping includes extrusion, pelletizing, beading, and/or spray drying. In some embodiments, spray drying or beading is generally used when the catalyst composition is used in slurry type reactor, fluidized beds, moving beds, expanded beds, or ebullating beds. For fixed bed applications, the catalyst composition may be extruded, pelletized or beaded. In fixed bed applications, prior to or during the shaping, any additives that facilitate the shaping may be used.

The resulting catalyst composition or more suitably the catalyst intermediate may be, after an optional drying step, be optionally calcined. Calcinations temperatures may range from about 100° C. to 600° C. or from about 350° C. to 500° C. for a time varying from 0.5 to 48 hours. In certain embodiments, the catalyst samples are calcined at temperatures ranging from 400° C. to 500° C. or from 500° C. to 700° C.

The resultant extrudates may be further loaded with active metals to obtain the desired active metal composition for the finished product. Such further loading is directly related to the desired metal loading, and the amount incorporated during or prior to the shaping stage of the material. For the same, various impregnation methods known in the art can be applied. Either the wet impregnation or the incipient impregnation may be used to load active metals. In an embodiment, the pore filling incipient impregnation method may be applied to load the Group VIB metal oxides. The method employed also may affect the pore size distribution of the finished catalyst, and hence the performance of the product. The material is again to be further thermal treated for the activation of the catalytic components.

In some embodiments, a double metal cyanide catalyst may be used alone or in combination with the Group IVB metal oxide catalyst described herein. One of metals of the double metal cyanide catalyst is $Zn^{2+}$ while the other is Fe. Co-existence of Zn and Fe in the active site linking through cyano bridges makes it efficient to transform feedstocks containing fatty acids in a single step to fatty acid esters. The catalyst could be separated easily by centrifugation or by simple filtration and reused. Double metal cyanide catalysts are described in U.S. Pat. Nos. 7,754,643 to Srinivas, U.S. Pat. No. 7,482,480 to Srinivas, U.S. Pat. No. 7,842,653 to Srinivas, which are incorporated herein by reference. For example, a double metal cyanide catalyst may be used alone or in combination with a molybdenum metal catalyst containing phosphorus as a promoter.

The catalysts described herein are highly efficient and are easily separated from the products for further re-use. In contrast, prior art catalysts may require treatment with mineral acid, alkali bases, and lipases which may increase costs of catalyst separation. The catalyst described herein is beneficial and leads to an economic and eco-friendly process. Hence, the solid catalysts described herein are not only efficient but avoid the tedious process of catalyst recovery characteristic of the prior art processes. The present catalyst system is efficient without using any additional solvent.

In batch processing to produce fatty acid alkyl esters, a fatty acid glyceride, an alcohol, and a solid catalyst are contacted to produce a reaction mixture. The catalyst used in a batch process may be a finely powdered catalyst. Although the catalyst may remain in a separate phase, or substantially separate phase from the fatty acid glyceride, alcohol and/or reaction products during contacting, the catalyst is separated from the liquid reaction mixture prior to the removal of methanol and/or glycerin using separation techniques known in the art. For example, centrifugation followed by simple decantation. The resulting catalyst free liquid reaction mixture may be separated by removal of excess alcohol through distillation techniques. Removal of the alcohol allows the fatty acid methyl esters to separate from remaining products. Fatty acid methyl esters may be separated from the reaction mixture by gravity separation or by contacting the reaction mixture with a non-polar solvent. In some embodiments, the non-polar solvent is petroleum ether.

In contrast to a batch process, the continuous process is used to produce bioproducts, as described herein, eliminates the need for catalyst separation and/or the saponification step used in conventional alkaline catalyst processes. The reaction may be conducted using minimal or substantially no solvent which reduces production of by-products and/or reduces costs of the process as compared to conventional processing. The process conditions allow for increased glycerol purity and fatty acid methyl ester yield as compared to products produced using conventional alkaline catalyst processing. The process described herein also reduces the formation of undesirable by-products, for example, glycerol methyl ethers.

In some embodiments, a mixture of fatty acid glyceride feedstock and alcohol is provided continuously to a reactor designed to operate at moderate temperatures and pressures. FIG. 1 is a schematic representation of a continuous process of an embodiment to produce fatty acid alkyl esters. The fatty acid glyceride feedstock may be stored in a permanent or movable tank (for example, totes). The fatty acid glyceride feedstock may be heated to enhance fluidity of the feedstock and reduce the risk of plugging lines with high melting feedstocks or feedstock mixtures, e.g. tallow. In some embodiments, the fatty acid glyceride feedstock is stored a temperature ranging from about 50° C. to about 90° C. or from about 60° C. to about 80° C. In some embodiments, the fatty acid glyceride feedstock is filtered to remove particulate and/or insoluble matter. The fatty acid glyceride feedstock may be analyzed to assess the amount of fatty acid glycerides, free fatty acids, and/or water in the fatty acid glyceride feedstock (for example, using near infrared spectrometry and/or Karl Fischer analysis for water). For example, amounts of oleic acid and triolein may be assessed in a fatty acid glyceride feedstock stream. The flow rate may be determined on a mass or molar ratio of the oleic acid to alcohol and/or triolein ratio to alcohol or a combination of the oleic acid and triolein to alcohol ratios.

Fatty acid glyceride feedstock stream 100 may be blended with alcohol stream 102 prior to entering the reactor to form a fatty acid glyceride/alcohol mixture. A temperature of fatty acid glyceride feedstock stream may range from 100° C. to 250° C. at a pressure from about 650 to about 750 psig (about 4.5 MPa to 5.2 MPa). In some embodiments, a temperature of fatty acid glyceride feedstock stream may range from 200° C. to 230° C. at a pressure from 650 to 880 psig (about 4.5 MPa to about 6 MPa). A continuous s flow rate of fatty acid glyceride feedstock stream 100 may range from about 0.1 Weight Hourly Space Velocity ("WHSV") to about 1 WHSV, from 0.3 to 0.8 WHSV, or from 0.5 to 0.7 WHSV. A temperature of alcohol stream 102 may range from 75° C. to 85° C. at a pressure from 650 to 750 psig (about 4.5 MPa to about 5.2 MPa). A flow rate of alcohol stream 102 may range from about 0.1 WHSV to about 1 WHSV, from 0.3 to 0.8 WHSV, or from 0.5 to 0.7 WHSV.

As fatty acid glyceride feedstock stream 100 from fatty acid glyceride feedstock storage unit 101 and alcohol stream 102 from alcohol storage unit 103 flow through mixer 104, the streams are mixed to form fatty acid glyceride feedstock/alcohol stream 106. In some embodiments, fatty acid glyceride feedstock/alcohol stream is an emulsion. Mixer 104 may be one or more in-line mixers or other known mixers. In some embodiments, the fatty acid glyceride feedstock and alcohol may be delivered continuously to the reactor as separate streams. Fatty acid glyceride feedstock/alcohol stream 106 may pass through heater 108 to raise the temperature of the stream to a temperature proximate the reaction temperature. For example, heater 108 may raise the temperature of fatty acid glyceride feedstock/alcohol stream 106 to about 220° C. at a pressure of 700 psig (about 4.8 MPa).

Fatty acid glyceride feedstock/alcohol stream 106 may enter reactor 110 and flow upward through the reactor. A flow rate of fatty acid glyceride feedstock/alcohol stream 106 may range from about 0.0.1 WHSV to about 1.0 WHSV, from 0.3 to 0.8 WHSV, or from 0.5 to 0.7 WHSV.

The flow rate of fatty acid glyceride feedstock/alcohol stream 106 through reactor 110 may be determined based on the assessed amount of fatty acid glycerides and/or alcohol in the fatty acid glyceride feedstock/alcohol stream. In some embodiments, a flow rate of the fatty acid glyceride feedstock/alcohol stream is determined based on a predetermined mole ratio of alcohol to free fatty acid. Reactor 110 may include over one or more heterogeneous catalysts. In some embodiments, the catalyst is a heterogeneous acidic catalyst. Contact of the feed streams with the catalyst produces a crude product. The crude product includes fatty acid alkyl esters, glycerin, water, unreacted glycerides and excess alcohol.

In some embodiments, the catalyst is fixed in the reactor. For example, the reactor may be a fixed bed reactor, a continuously stirred tank reactor, fluidized bed reactor or an ebullating bed reactor. Other designs to allow continuous flow of the fatty acid glyceride feedstock stream, alcohol stream, the fatty acid glyceride feedstock/alcohol stream or mixtures thereof over the catalyst and through the reactor may be contemplated. In some embodiments, the catalyst may be activated prior to introducing feedstocks into the reactor by introducing a heated stream of dry inert gas (for example, nitrogen) into the contacting zones at a known space velocity (SV=vol $N_2$/hr divided by vol of catalyst) at atmospheric pressure. For example, a catalyst may be placed in a reactor heated with a dry nitrogen stream at a space velocity of 500/hr at atmospheric pressure. Activating the catalyst may involve heating the reactor contents to remove residual water, which promotes hydrolysis. In some embodiments, the catalyst may be heated at different temperatures for set periods of time. For example, the catalyst may be heated to 200° C. under a nitrogen gas sweep and help for 6 hours and then heated to 250° C. and held at 250° C. for four hours. The heating cycle may be repeated until less than 1 ppm of water or no water is detected in the catalyst. The temperature of the reactor may be reduced under the inert atmosphere to a temperature of less than about 150° C.

Temperatures in reactor 110 may range from about 165° C. to about 260° C. or from 190° C. to 210° C. at a pressure ranging from 10 psig to 800 psig (from about 0.21 MPa to about 5.5 MPa). Operating pressures greater than atmospheric pressure may create a single, continuous liquid phase of the reagents within reactor 110. Such condition of the fatty acid glycerides and the alcohol aids the kinetics of the process. Thus, the alcohol may be maintained in a liquid state and a higher reaction rate is achieved. Flow of fatty acid glyceride feedstock/alcohol stream 106 through reactor 110 may range from about 0.1 WHSV to about 1.0 WHSV, from 0.3 to 0.8 WHSV, or from 0.5 to 0.7 WHSV.

In some embodiments, the process stream is monitored. For example, the absence or appearance of products may be monitored using near infrared spectrometry. During the continuous process, real-time monitoring of the changes in the data (for example, changes in the near infrared spectrum) within the process at critical points provides data continuously on the relative concentrations of fatty acid glycerides, glycerides, fatty acid alkyl esters, glycerin and other components. Based on the assessment of the monitored relative concentrations, adjustments to process conditions may inhibit by-product formation and/or allow production of high quality fatty acid alkyl esters. Based on the monitored conditions, adjustments may not be necessary.

In some embodiments, data from one or more continuous processes may be collected continuously or at specified intervals and compiled into data sets. Such data sets include a) conversion data for various fatty acid glyceride feedstocks to fatty acid alkyl esters, b) catalyst aging, c) fatty acid glyceride feedstock selection (for example, selection based on the content of free fatty acid in feed and/or other impurities in the fatty acid glyceride feedstock), d) product quality, both for fatty acid alkyl esters and glycerin, e) purity of recycled alcohol, f) composition of fatty acid alkyl esters and the fatty acid alkyl esters distillation residues and g) the quality of final product. Other types of data may be collected, as necessary. Data may be collected from one or more process steps and compared across locations, time periods and age of facilities, among other factors. The stored data may be compared and conditions may be adjusted over time based on fatty acid glyceride feedstock and fatty acid glyceride feedstock suppliers, the seasonal variation in renewable fatty acid glyceride feedstocks and other operating parameters. In some embodiments, one or more process conditions at one or more locations are adjusted to maintain or improve the quality of the products produced, based on collected data.

Assessing the collected data continuously and in real-time allows assessment of small changes in reaction parameters on total system performance and to adjust these parameters to produce high quality fatty acid alkyl esters. Collecting data may include sending data to a remote server that includes data from the system and other system in a data management system. The data may be compared to other systems and adjustments may be made depending on the assessment of the data. For example, based on the data, the flow rate, temperature, pressure, or mole ratio of methanol to total fatty acid glycerides may be adjusted to increase fatty acid alkyl ester conversion at one or more locations. Additional adjustment points include flow rate, varying pressure and temperature across an alcohol flash evaporator to achieve alcohol recycled economics, and flow rate, distillation take over ratio (ratio of the mass of recovered condensate in a distillation to the mass of the undistilled material) and vacuum in short-path distillation to achieve high quality products. Assessment and adjustment of parameters may lower costs in producing products, thus making production of bioproducts economically feasible. In some embodiments, real time monitoring provides information about the formation of by-products from side reactions. For example, water content in the reactor may be monitored. Production of an excess amount of water may promote hydrolysis of the fatty acid alkyl ester product to alcohols and fatty acids. Based on the assessment of the water content in the reaction mixture, conditions may be adjusted to minimize the amount of water produced during the process.

Pressurized crude product stream 112 may exit reactor 110 at desired flow rate and pressure to maintain continuous operation of reactor 110. For example, crude product stream 112 may exit reactor 110 at a temperature of about 200° C. to about 205° C. and a pressure of about 880 psig (about 6.0 MPa). A flow rate of pressurized crude product stream 112 may range from about 0.1 WHSV to about 1.0 WHSV, from 0.3 to 0.8 WHSV, or from 0.5 to 0.7 WHSV. Pressurized crude product stream 112 flows through one or more pressure reduction devices 114 and one or more heat exchangers 116. Pressure reduction device 114 rapidly drops the pressure of the pressurized crude product stream 112. For example, pressure reduction device may rapidly drop the pressure of crude product stream 112 to about 5 psig (about 0.034 MPa). Heat exchanger 116 maintains the temperature of the pressurized stream at a desired temperature (for example, a temperature of about 70° C. to about 80° C.). During the rapid pressure drop of the crude product stream some methanol and water may be removed from the crude product stream. Pressure reduction device 114 may maintain a desired pressure in the reactor while releasing fluid (for example, volatile components, alcohol and water) from reactor 110.

Under reduced pressure, the crude product stream 118 enters separation unit 120, a pressure of the stream may be rapidly reduced. In some embodiments, separation unit 120 is a separation unit which operates under a slight vacuum, that removes components having a boiling point of less than 100° C. (for example, methanol, ethanol and/or water) to be rapidly removed. In some embodiments, separation unit 120 is a flash evaporation unit which operates under a slight vacuum, enabling low boiling alcohols (for example, methanol and ethanol) and other volatiles (for example, water) to be rapidly removed (flashed). The distilled or flash evaporated components may be collected. An average temperature of low pressure crude product stream 118 may be less than 100° C. or between about 70° C. and about 80° C. at 6.4 psig (0.065 MPa) as the crude product stream enters separation unit 120. A flow rate of low pressure crude product stream 118 may be about 146.6 lb/hr (about 66.5 kg/hr) or about 0.4 WSHV. Rapid reduction of pressure of crude product stream 118 may be induced by creating a pressure differential in separation unit 120 by using pump 123. For example, applying vacuum to the top of separation unit 120 until a pressure of about 0.065 MPa is reached. A sudden drop in pressure may induce rapid distillation (evaporation) of the excess alcohol and water from the crude product. Methanol/water stream 122 may exit separation unit 120 transported to one or more recovery tanks. A portion of methanol/water stream 122 (stream 122') may be mixed with fatty acid glyceride feedstock stream 100 and/or alcohol stream 102. Analysis of the methanol/water stream 122 may be done (for example, using near infrared spectrometry) to determine the amount, if any, of glycerin and/or fatty acid alkyl ester in the methanol/water stream. Based on the analysis the methanol/water stream may be subjected to further treatment to recover the glycerin and/or fatty acid and/or increase the amount of methanol in the stream. In some embodiments, the methanol/water stream may be primarily water and thus treated as waste water after distillation of the methanol for recycle to 103.

Rapid distillation (for example, flash evaporation) removes the excess alcohol and water under mild thermal conditions. During rapid evaporation, the crude fatty acid alkyl ester undergoes minimal or no thermal degradation during the distillation process. Thus, fewer by-products and a higher quality product are produced as compared to conventional processing to produce fatty acid alkyl esters. During rapid evaporation, the temperature of the crude stream may be increased to assist in rapid evaporation of the alcohol, water, and other volatiles in the crude product stream. Due to the sudden loss of pressure, low boiling alcohols and water evaporate rapidly (flash) and thereby cool the residual effluent. The recovered alcohol can be refined in a separate distillation system for reuse, as needed, in the reactor.

Crude fatty acid ester/glycerin product stream 124 may enter separator 126. In separator 126, glycerin stream 128 and crude fatty acid ester stream 130 may be separated from the crude fatty acid ester/glycerin product stream 124. For example, a crude fatty acid ester stream may be separated from a glycerin stream using liquid-liquid centrifugation, gravity-based decantation and dynamic centrifugation or other methods familiar to those skilled in the art. In some embodiments, the fatty acid ester stream is separated from the glycerin stream using gravity-based, electrostatically enhanced separation techniques.

In some embodiments, separator 126 is an electrostatic separator. In some embodiments, the crude fatty acid ester/glycerin product stream 124 may be analyzed using near infrared spectrometry to determine an amount of water in the stream prior to the stream entering the separator. The crude fatty acid ester/glycerin product stream may have a water content of less than 2 percent by weight. In an electrostatic separator an electric field (for example, direct current and/or alternating current) may be applied to crude fatty acid ester/glycerin product stream 124 to separate glycerin from crude fatty acid ester stream 124. The separated glycerin stream may have a purity of greater than 98% by weight.

Crude fatty acid alkyl ester stream 130 may be further purified to meet product specifications. In some embodiments, crude fatty acid alkyl ester stream 130 is used as is for diesel fuel. As shown in FIG. 1, crude fatty acid alkyl ester stream 130 enters distillation unit 132. In distillation unit 132, crude fatty acid alkyl ester stream 130 is distilled to produce fatty acid alkyl ester product stream 134 and bottoms stream 136. Distillation units may include, but is not limited to, wiped-film evaporator or another short-path distillation unit. Fatty acid alkyl ester product stream 134 may contain substantially fatty acid methyl ester and, thus be used for biofuel without further treatment. Fatty acid alkyl ester product stream 134 may be light colored, substantially water white or water white. In some embodiments, the distilled fatty acid alkyl ester product stream is passed through one or more resin beds to produce a high purity, biodiesel product.

In some embodiments, bottoms stream 136 includes polyunsaturated fatty acid alkyl esters (for example, polyunsaturated fatty acid methyl esters). The polyunsaturated fatty acid alkyl acids are derived from polyunsaturated fatty acids present in the starting feedstock (for example, feedstock 101 in FIG. 1). Polyunsaturated fatty acid alkyl esters may be hydrolyzed to produce high purity polyunsaturated fatty acids (for example, omega 3 fatty acids and omega 6 fatty acids).

In some embodiments, crude fatty acid alkyl ester stream 130 is a fatty acid methyl ester stream. At least a portion of the crude fatty acid alkyl ester stream may be diverted and used to make biolubricants, heat transfer fluids, hydraulic fluids, gear oils or engine oils in a separate reactor. The ability to make biodiesel and biolubricants at the same facility without changing the catalyst or significantly altering the production equipment reduces operating costs.

Figure 2:
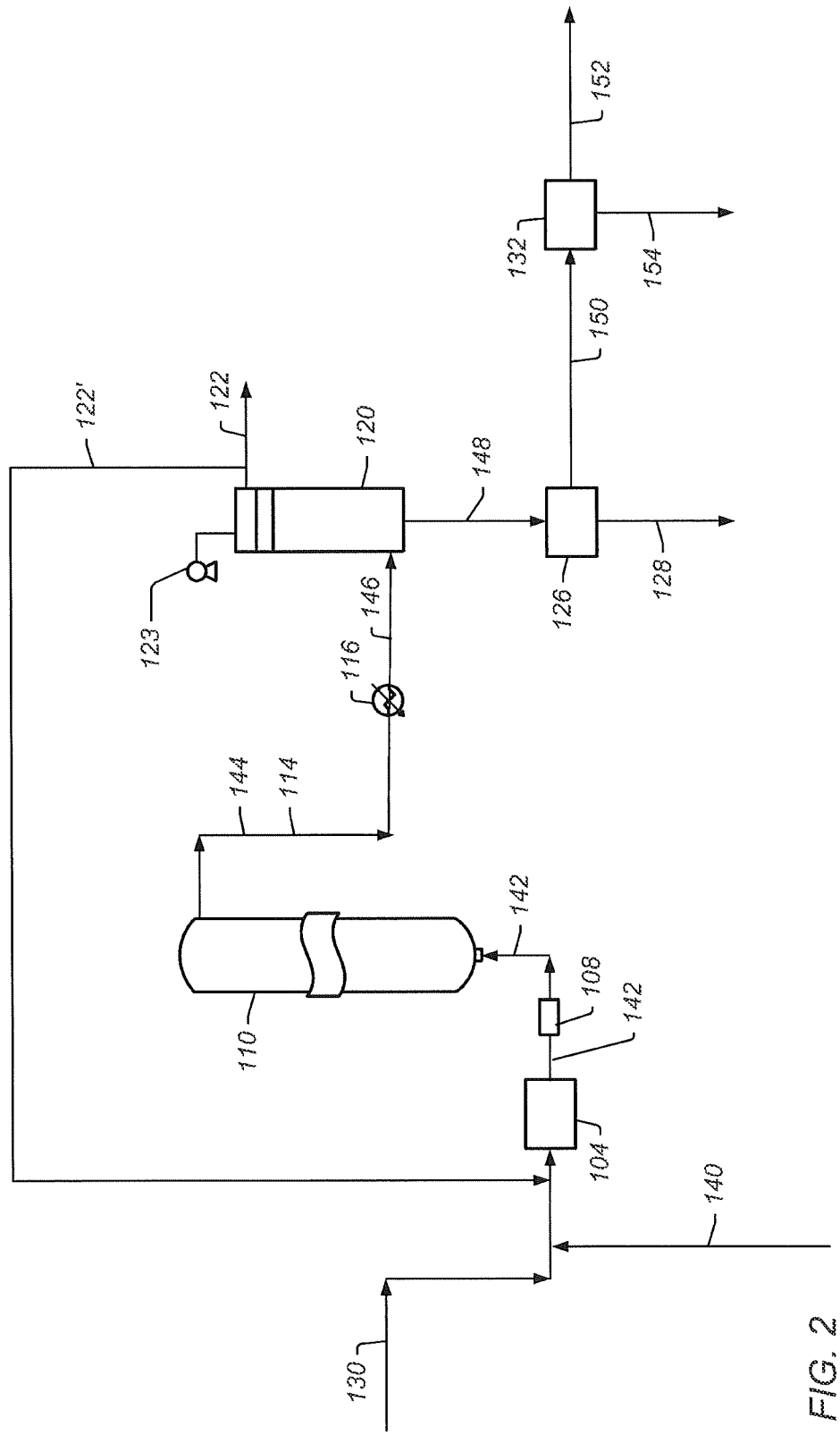
FIG. 2 illustrates one exemplary embodiment of a continuous process for producing fatty acid alkyl esters.

As shown in FIG. 2, crude fatty acid methyl ester stream 130 may be mixed with high boiling alcohol stream 140 (for example, alcohol stream having a carbon number greater than 6) in mixer 104. Fatty acid glyceride feedstock/alcohol stream 142 may pass through heater 108 to raise the temperature of the stream to a temperature proximate the reaction temperature. For example, heater 108 may raise the temperature of fatty acid glyceride feedstock/alcohol stream 142 to about 220° C. at a pressure of 1-2 psig (about 0.01 to 0.02 MPa).

Fatty acid glyceride feedstock/alcohol stream 142 may enter reactor 110 and flow upward through the reactor. A flow rate of fatty acid glyceride feedstock/alcohol stream 142 may range from about 0.1 WHSV to about 1.0 WHSV, from 0.3 to 0.8 WHSV, or from 0.5 to 0.7 WHSV. Reactor 110 may include over one or more heterogeneous catalysts. In some embodiments, the catalyst is a heterogeneous acidic catalyst. In certain embodiments, the catalyst is a double metal cyanide catalyst. Contact of the feed streams with the catalyst produces a crude product. The crude product includes fatty acid alkyl esters, glycerin, water, unreacted glycerides and excess alcohol. The ester portion of the fatty acid alkyl esters may have a carbon number greater than or equal to 5.

Temperatures in reactor 110 may range from about 65° C. to about 260° C. or from 90° C. to 2010° C. at a pressure ranging from 1 psig to 2 psig (from about 0.01 MPa to about 0.014 MPa). In some embodiments, temperatures in reactor 110 may range from about 65° C. to about 200° C. or from 90° C. to 205° C. at a pressure ranging from 1 psig to 2 psig (from about 0.01 to about 0.014 MPa). Continuous flow of fatty acid glyceride feedstock/alcohol stream 142 through reactor 110 may be controlled to produce a desired amount of crude product in a desired amount of time. For example, a flow of fatty acid glyceride feedstock/alcohol stream 142 through reactor 110 ranges from about 0.1 WHSV to about 1.0 WHSV, from 0.3 to 0.8 WHSV, or from 0.5 to 0.7 WHSV. Real-time analysis of the feed streams, crude product streams and/or methanol/water streams as described herein may be performed to assess reaction conditions and/or concentrations of components in the various streams so that formation of by-products is minimized.

Crude product stream 114 may exit reactor 110 at a temperature between 65° C. and about 200° C. and a pressure of about 1 psig to about 2 psig (about 0.1 MPa to 0.2 MPa). The crude product stream 114 flows through one or more heat exchangers 116. A flow rate of crude product stream 114 may range from about 0.1 WHSV to about 1.0 WHSV, from 0.3 to 0.8 WHSV, or from 0.5 to 0.7 WHSV. Heat exchanger 116 maintains the temperature of the reactor effluent stream from about 65° C. to about 220° C.

As crude product stream 146 enters separation unit 120, which is held under reduced pressure, 486 mmHg, (0.0.65 MPa), the excess of volatile alcohols may be removed (flashed or distilled depending on the boiling point of the alcohol), and leave crude biolubricant.

A temperature of crude product stream may be between about 70° C. and about 80° C. as the stream enters separation unit 120. A flow rate of low pressure crude product stream may be about 146.6 lb/hr (about 66.5 kg/hr) or about 0.4 WHSV. Rapid reduction of pressure may be induced by creating a pressure differential in separation unit 120 using pump 123 for example, reducing the pressure at the top of separation unit 120 to about 0.065 MPa. In separation unit 120 a temperature of the reaction mixture may be less than 100° C. at about 0.065 MPa. A sudden drop in pressure may induce rapid distillation (evaporation) of the excess alcohol and water from the crude product. Recovered alcohol stream 122 may exit separation unit 120 transported to one or more recovery tanks. A portion of the recovered stream 122 (stream 122') may be mixed with fatty acid glyceride feedstock stream 130_and/or alcohol stream 140.

Rapid distillation (for example, flash distillation) removes the excess alcohol and water under mild thermal conditions. During rapid distillation, the crude fatty acid alkyl ester undergoes minimal or no thermal degradation during the distillation process. Thus, fewer by-products and a higher quality product are produced as compared to conventional processing to produce fatty acid alkyl esters. During rapid distillation, the temperature of the crude fatty acid alkyl ester stream may be increased to assist in rapid evaporation of the alcohol, water and other volatiles in the crude product stream. Due to the sudden loss of pressure, low boiling alcohols and water evaporate rapidly (flash) and thereby cool the residual effluent. The recovered alcohol may be purified in a separate distillation system for reuse, as needed, in the reactor.

In some embodiments, the alcohol is not volatile enough to permit flash evaporation in separation unit 120. The excess alcohol in the reactor effluent stream will be removed by aqueous extraction by means known to those skilled in the art of liquid-liquid extractions. The resulting crude high boiling ester may be purified as needed to meet industry specifications for use as biodegradable lubricant base oils.

Crude fatty acid alkyl ester product stream 148 may enter separator 126. In separator 126, an aqueous stream 128, containing excess alcohol or polyol and crude fatty acid alkyl ester stream 150 may be separated from the crude fatty acid alkyl ester/glycerin (for example, crude biolubricant) product stream 148 using conventional techniques of liquid-liquid extraction.

In embodiments when glycerin is present in the crude fatty acid alkyl ester stream, separator 148 is an electrostatic separator. In an electrostatic separator an electric field may be applied to crude biolubricant product stream 148 to separate glycerin from crude fatty acid alkyl ester stream 150. The separated glycerin stream may have a purity of greater than 98% by weight.

Crude fatty acid alkyl ester stream 150 may be further purified to meet ASTM or commercial product specifications. Crude fatty acid alkyl ester stream 150 may enter distillation unit 132 (for example, a vacuum distillation unit). In distillation unit 132, crude fatty acid alkyl ester (for example, biolubricant) stream 150 is distilled to produce a finished product stream 152 and bottoms stream 154. In some embodiments, fatty acid alkyl ester stream 152 is suitable for use as biolubricants, heat transfer fluids and hydraulic fluids, such as 2-cycle engine oil. In some embodiments, distillation unit 132 and separation unit 126 are the same unit.

In some embodiments, when making fatty acid alkyl esters in a continuous manner low amounts of alcohol may be entrained in the final product (for example, less than 1% of alcohol may remain fatty acid alkyl ester/glycerin crude product and/or the fatty acid alkyl ester product). Fatty acid alkyl ester product containing alcohol (for example, methanol) may not meet biodiesel or other bioproduct specifications. Thus, further purification steps may be required to obtain a product that meets biodiesel and/or other product specifications. Furthermore, residual alcohol may permit the retention of moisture in the hydrocarbon (oil) phase) which can promote hydrolysis of the fatty acid alkyl ester to fatty acid and alcohol upon storage.

To remove the alcohol from the reaction mixture to the lowest possible level, the separation unit may include an internal heat exchanger in an upper portion of the separation unit. Incorporation of the heat exchanger may allow for all or substantially all of the alcohol/water to be removed continuously or substantially continuous from the reaction effluent mixture. For example, a fatty acid methyl ester product may have an alcohol (for example, methanol) content of less than 100 ppm, less than 10 ppm, less than 1 ppm, or less. A temperature of the heat exchanger may be greater than the boiling point of the alcohol and/or water in the reaction mixture at the operating pressure (for example, greater than 65° C. at about 0.065 MPa (about 486 mm Hg). As the reaction mixture enters the alcohol separation unit, alcohol and/or water may be removed under vacuum while the higher boiling components (for example, crude fatty acid alkyl ester/glycerin mixture) are cooled by the condenser. The higher boiling components may settle to a bottom portion of the alcohol separation unit and be collected. Collecting fatty acid alkyl ester/glycerin mixture under reduced pressure may allow any entrained alcohol to be removed from the mixture through a degassing process. The fatty acid alkyl ester/glycerin mixture may collect in the alcohol separation unit until a desired level of the mixture is obtained. The mixture may then be moved (for example, pumped) to a fatty acid alkyl ester/glycerin separator. In some embodiments, the higher boiling components are pumped directly to a fatty acid alkyl ester/glycerin separator.

In some embodiments, during collection of the fatty acid alkyl ester/glycerin mixture, glycerin may separate from the fatty acid alkyl ester/glycerin mixture. The separated or at least a part of the separated glycerin may be removed from the separator as a separate stream (for example, the glycerin my settle to a bottom portion of the separator). In some embodiments, the separated glycerin may include some fatty acid alkyl ester. The separated glycerin may be further treated as described herein to separate fatty acid alkyl ester from the glycerin.

Figure 3:
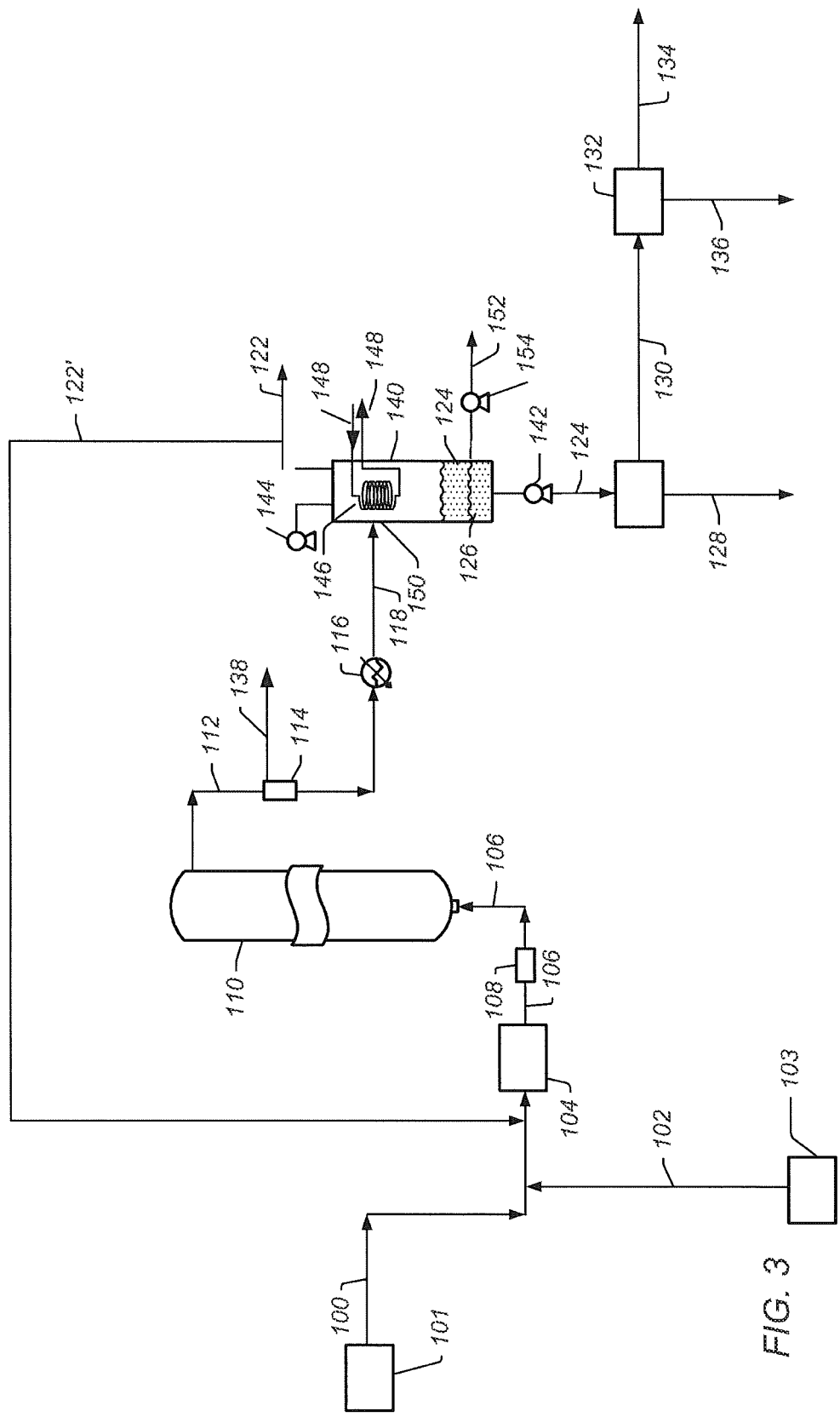
FIG. 3 illustrates one exemplary embodiment of a continuous process for producing fatty acid alkyl esters.

FIG. 3 depicts a schematic of using an alcohol separator in a continuous process. As fatty acid glyceride feedstock stream 100 from fatty acid glyceride feedstock storage unit 101 and alcohol stream 102 from alcohol storage unit 103 flow through mixer 104, the streams are mixed to form fatty acid glyceride feedstock/alcohol stream 106. In some embodiments, fatty acid glyceride feedstock/alcohol stream is an emulsion. Mixer 104 may be one or more in-line mixers or other known mixers. In some embodiments, the fatty acid glyceride feedstock and alcohol may be delivered continuously to the reactor as separate streams. Fatty acid glyceride feedstock/alcohol stream 106 may pass through heater 108 to raise the temperature of the stream to a temperature proximate the reaction temperature. For example, heater 108 may raise the temperature of fatty acid glyceride feedstock/alcohol stream 106 to about 220° C. at a pressure up to 880 psig (about 6.1 MPa).

Fatty acid glyceride feedstock/alcohol stream 106 may enter reactor 110 and flow upward through the reactor. A flow rate of fatty acid glyceride feedstock/alcohol stream 106 may range from about 0.0.1 WHSV to about 1.0 WHSV, from 0.3 to 0.8 WHSV, or from 0.5 to 0.7 WHSV.

The flow rate of fatty acid glyceride feedstock/alcohol stream 106 through reactor 110 may be determined based on the assessed amount of fatty acid glycerides and/or alcohol in the fatty acid glyceride feedstock/alcohol stream. In some embodiments, a flow rate of the fatty acid glyceride feedstock/alcohol stream is determined based on a predetermined mole ratio of alcohol to free fatty acid. Reactor 110 may include over one or more heterogeneous catalysts. In some embodiments, the catalyst is a heterogeneous acidic catalyst. Contact of the feed streams with the catalyst produces a crude product. The crude product includes fatty acid alkyl esters, glycerin, water, unreacted glycerides and excess alcohol.

In some embodiments, the catalyst is fixed in the reactor. For example, the reactor may be a fixed bed reactor, a continuously stirred tank reactor, fluidized bed reactor or an ebullating bed reactor. Other designs to allow continuous flow of the fatty acid glyceride feedstock stream, alcohol stream, the fatty acid glyceride feedstock/alcohol stream or mixtures thereof over the catalyst and through the reactor may be contemplated.

Average Temperature in reactor 110 may range from about 165° C. to about 260° C. or from 190° C. to 210° C. at an average pressure ranging from 10 psig to 880 psig (from about 0.21 MPa to about 6.1 MPa). In some embodiments, the reactor has an average temperature is 210° C. and average pressure of 5.1 MPa. Operating pressures greater than atmospheric pressure may create high-shear of the fluid in reactor 110. High shear may emulsify the fatty acid glycerides and the alcohol and form a quasi single-phase liquid system. Thus, the alcohol may be maintained in a liquid state and a higher reaction rate is achieved. Flow of fatty acid glyceride feedstock/alcohol stream 106 through reactor 110 may range from about 0.1 WHSV to about 1.0 WHSV, from 0.3 to 0.8 WHSV, or from 0.5 to 0.7 WHSV.

Pressurized crude product stream 112 may exit reactor 110 at desired flow rate and pressure to maintain continuous operation of reactor 110. For example, crude product stream 112 may exit reactor 110 at an average temperature from about 200° C. to about 205° C. and an average pressure from about 10 psig to 880 psig (about 0.21 MPa to about 6.1 MPa). A flow rate of pressurized crude product stream 112 may range from about 0.1 WHSV to about 1.0 WHSV, from 0.3 to 0.8 WHSV, or from 0.5 to 0.7 WHSV. Pressurized crude product stream 112 flows through one or more pressure reduction devices 114 and one or more heat exchangers 116. Pressure reduction device 114 rapidly drops the pressure of the pressurized crude product stream 112. For example, pressure reduction device may rapidly drop the press of pressurized crude product stream 112 to about 5 psig (about 0.034 MPa). Pressure reduction device 114 may maintain a desired pressure in the reactor while releasing fluid (for example, volatile components, alcohol and water) from reactor 110. In some embodiments, pressure reduction device 114 is a back pressure valve.

Heat exchanger 116 maintains the temperature of the pressurized stream at a desired temperature (for example, a temperature of about 70° C. to about 80° C.). During the rapid pressure drop of the crude product stream some or a majority of the methanol and water may be removed from the crude product stream. In some embodiments, a majority or a substantial amount of methanol and water may be removed from the crude product stream via conduit 138. In some embodiments, conduit 138 is connected to an alcohol recovery unit.

As low pressure crude product stream 118 enters alcohol separation unit 140, a pressure of the stream may be rapidly reduced. For example, the pressure of the stream may be reduced from an average pressure of 6.1 MPa to about 0.065 MPa. A temperature of low pressure crude product stream 118 may be about 70° C. at an average pressure of 486 mmHg (0.065 MPa) as the crude product stream enters alcohol separation unit 140. A flow rate of low pressure crude product stream 118 may be adjusted using pump 142. Alcohol separation unit 140 includes heat exchanger 146. Cooling fluid may be circulated in heat exchanger 146 (shown by arrows 148). The heat exchanger may be maintained at an average temperature higher than the boiling point of the alcohol being removed from the alcohol separation unit (for example, greater than 65° C. at 0.065 MPa). Reduction of pressure of crude product stream 118 is induced by creating a pressure differential in alcohol separation unit 140 using vacuum pump 144. For example, using pump 144 to apply vacuum to the top of alcohol separation unit 140 until a pressure of about 0.04 MPa is reached.

A drop or sudden drop in pressure (for example, pulling a vacuum on the reactor effluent stream) may induce rapid distillation (evaporation) of the excess alcohol and water from the crude product. Methanol/water stream 122 may exit separation unit 140 transported to one or more recovery tanks. A portion of methanol/water stream 122 (stream 122') may be mixed with fatty acid glyceride feedstock stream 100 and/or alcohol stream 102. Analysis of the methanol/water stream 122 may be done (for example, using near infrared spectrometry) to determine the amount, if any, of glycerin and/or fatty acid alkyl ester in the methanol/water stream. Based on the analysis the methanol/water stream may be subjected to further treatment to recover the glycerin and/or fatty acid and/or increase the amount of methanol in the stream. In some embodiments, the methanol/water stream may be primarily water and thus treated as waste water.

Rapid distillation (for example, flash evaporation) removes the excess alcohol and water under mild thermal conditions. During rapid distillation, the crude fatty acid alkyl ester undergoes minimal or no thermal degradation during the distillation process. Thus, fewer by-products and a higher quality product are produced as compared to conventional processing to produce fatty acid alkyl esters. During rapid distillation, the temperature of the crude stream may be increased to assist in rapid evaporation of the alcohol, water, and other volatiles in the crude product stream. Due to the sudden loss of pressure, low boiling alcohols and water evaporate rapidly (flash) and thereby cool the residual effluent. The recovered alcohol can be refined in a separate distillation system for reuse, as needed, in the reactor.

As crude product steam 118 contacts the heat exchanger, crude fatty acid alkyl ester/glycerin mixture 124 cools and collects in a bottom portion of alcohol separation unit 140. Collection of the fatty acid alkyl ester and glycerin under reduced pressure may allow the entrained alcohol to be removed from the crude fatty acid alkyl ester/glycerin mixture 124. Pump 142 may be connected to a level controller (not shown) which monitors the level of crude fatty acid alkyl ester/glycerin mixture 124 collecting in alcohol separation unit 140. When the level of crude fatty acid alkyl ester/glycerin mixture 124 reaches a desired level as indicated by level controller, pump 142 may engage and move a portion of crude fatty acid alkyl ester/glycerin mixture 124 from alcohol separation unit 140.

Upon standing, glycerin layer 150 may further separate from fatty acid alkyl ester/glycerin mixture 124. If sufficient glycerin separates from crude fatty acid alkyl ester/glycerin mixture 124, glycerin stream 152 may be removed from alcohol separation unit 140 using pump 154.

Crude fatty acid ester/glycerin product stream 124 may enter separator 126. In separator 126, glycerin stream 128 and crude fatty acid ester stream 130 may be separated from the crude fatty acid ester/glycerin product stream 124. For example, crude fatty acid ester stream 130 may be separated from a glycerin stream 128 using a liquid-liquid decanter. In an embodiment, crude fatty acid ester stream 130 may be separated from a glycerin stream 128 using a liquid-liquid decanter in parallel with an electrostatic precipitator.

In some embodiments, crude fatty acid alkyl ester stream 130 is a fatty acid methyl ester stream. At least a portion of the crude fatty acid alkyl ester stream may be used to make biolubricants, heat transfer fluids, or engine oils. The ability to make biodiesel and biolubricants at the same facility without changing the catalyst or significantly altering the production equipment reduces operating costs.

Crude fatty acid alkyl ester stream 130 may be further purified to meet product specifications. In some embodiments, crude fatty acid alkyl ester stream 130 is used as is for diesel fuel. Crude fatty acid alkyl ester stream 130 enters distillation unit 132. In distillation unit 132, crude fatty acid alkyl ester stream 130 is distilled to produce fatty acid alkyl ester product stream 134 and bottoms stream 136. Distillation units may include, but is not limited to, wiped-film evaporator or another short-path distillation unit. Fatty acid alkyl ester product stream 134 may contain substantially fatty acid methyl ester and, thus be used for biofuel without further treatment. Fatty acid alkyl ester product stream 134 may be light colored, substantially water white or water white. In some embodiments, the distilled fatty acid alkyl ester product stream is passed through one or more resin beds to produce a high purity, biodiesel product.

In some embodiments, bottoms stream 136 includes polyunsaturated fatty acid alkyl esters (for example, polyunsaturated fatty acid methyl esters). The polyunsaturated fatty acid alkyl acids are derived from polyunsaturated fatty acids present in the starting feedstock (for example, feedstock 100). Polyunsaturated fatty acid alkyl esters may be hydrolyzed to produce high purity polyunsaturated fatty acids (for example, omega 3 fatty acids and omega 6 fatty acids) as described herein.

In some embodiments, one or more parameters of the continuous process are controlled using automated controllers, for example, a computer. The methods described herein may also be embodied on a computer readable medium and in a controller. One or more controllers may be coupled to one or more mixing devices, one or more reactors, one or more separation devices, and or one or more distillation devices. The controllers may be coupled to a computer that includes a computer readable medium. The computer readable medium may include the parameters for making bioproducts using continuous systems. For example, the computer may include storage devices that are accessible by the computer readable medium. The storage devices may include look-up tables and/or databases that include, but are not limited to, data associated with flow rates, molar ratios, temperatures, pressures, fatty acid concentrations in the feedstock or alcohol molecular weights, fatty acid glyceride molecular weights, or other such data. One or more parameters may be displayed on a controller or a display device coupled to the computer during the operation of the process.

In some embodiments, each unit of the continuous system may have an input and an output. For example, inputs may be coupled to a fatty acid glyceride supply unit and/or an alcohol stream supply units and outputs coupled to the reactor. A controller may be coupled to a valve of one of the supply units. The mixing device, reactor, distillation units, and/or separation units are monitored for fluid flowing through them. When fluid flow or mass flow is detected through one or more of the units in the process, the controllers coupled to the valves may send a signal such that the valve position is adjusted until flow of fluid through the system (for example, the flow of the feedstock stream from a mixing device to the reactor, and/or the flow from the reactor to the distillation unit) meets the desired parameters.

EXAMPLES

Non-limiting examples are described herein.

Example 1

Batch

Palm oil (2.99 kg) and methanol (1.61 kg) were charged to a 20 L stainless steel vessel. To this was added, with stirring, 0.15 kg of double metal cyanide powdered catalyst (5% by wt.). The vessel was sealed and temperature increased to 170° C. with agitation and held with agitation for eight (8) hrs. Upon cooling and filtration, a total of 4.451 kg of material was recovered. Following the distillation of excess methanol, the fatty acid methyl ester (FAME) and glycerin layers were separated, affording 0.316 kg of glycerin (99.5% by wt) and 4.135 kg FAME (99.5% by wt).

Example 2

Batch

A batch reaction for producing fatty acid methyl esters (bio-diesel) from soybean oil and methanol was conducted in a "Teflon-lined" steel autoclave (100 ml) and using a rotating hydrothermal reactor (Hiro Co., Japan; Mode-KH 02). The rotation speed was 50 rpm. A soybean oil (33 grams), methanol and "finely powdered" solid alumina catalyst (5 wt % based on grams of soybean oil, containing 14.9% by weight molybdenum trioxide and 2% by weight phosphorus) were sealed in a reactor and heated at 190° C. for 8 hours. The alcohol to oil molar ratio was 15:1. The autoclave was cooled to room temperature. The catalyst was separated by centrifugation followed by simple decantation. The entire liquid was subjected to vacuum distillation and excess, unused alcohol was removed. Glycerol settled at the bottom as a separate layer. Fatty acid methyl esters and un-reacted oil, if any, floated above the glycerol portion. Petroleum ether (20 to 50 ml) was then, added. The esters and oil readily went into the petroleum ether layer. Glycerol remained as a separate layer. It was separated and its yield was determined and purity checked by $^1$H nuclear magnetic resonance (Bruker 200 MHz Avance NMR spectrometer). The conversion to fatty acid methyl ester was 100%. The fatty acid alkyl ester portion contained 95.6% fatty acid methyl ester, 0% triglyceride, 0.5% diglyceride, and 4.0% monoglyceride as determined by high performance liquid chromatography (HPLC).

Example 3

Continuous Process

In a fixed bed reactor (D×ID=3"×24"), a bed of a alumina supported catalyst (1,341 g) containing 14.9% by weight molybdenum oxide ($MoO_3$), 2% by weight phosphorus (P), and inert alumina balls (540 g, Denstone® D99, Norpro, Saint Gobain, Ohio, U.S.A.) in a 2.5:1 ratio in the form of extrudates is placed in a stainless steel reactor having a provision of auto-controlled temperature and feed-flow facilities. As methanol and fatty acid glyceride feedstock are immiscible, a duel pumping system was utilized and the feedstock was sent in an upward-flow at a WHSV of 0.7. The mass ratio of methanol to fatty acid glyceride feedstock was maintained at 0.54. The operating temperature of the reactor was maintained at 216° C. and the pressure of 45 bar. The reaction conditions and mass ratio were maintained over a period of 10 days. The product was collected at the top of the reactor. The entire liquid was subjected to vacuum distillation and excess, unused alcohol was removed. The crude product was separated from the glycerin in a separatory funnel. TABLE 1 lists the fatty acid glyceride feedstock and the crude product analysis.

TABLE 1

| Fatty Acid Glyceride feedstock | Pressure, bar | Temp., ° C. | WSHV, $hr^{-1}$ | Product composition, wt % by HPLC | | | |
|---|---|---|---|---|---|---|---|
| | | | | Tri-glycerid | Di-glycerid | Mono-glycerid | Fatty acid methyl |
| RBD soy oil | 45 | 216 | 0.7 | 0.04 | 0.03 | 0.38 | 99.55 |
| Corn Oil | 45 | 216 | 0.7 | 0.99 | 0.51 | 0.49 | 98.01 |
| DG Cottonseed | 45 | 216 | 0.7 | 0.69 | 0.43 | 0.48 | 98.40 |

RDB soy oil is refined, bleached and deodorized soy oil. DG Cottonseed is degummed cottonseed oil.

The crude product was distilled in a glass wiped film evaporator to afford water white fatty acid methyl ester with a total fatty acid glycerides value of less than 0.17. The distilled product met the ASTM D6584 specifications for biodiesel.

Continuous. The production of fatty acid octyl ester (biolubricants) by esterification of a crude fatty acid octyl ester derived from soybean oil with octanol is described herein. The reaction was conducted in a similar manner as described in Example 2. Over a period of 2 days soy oil was contacted with an alumina supported catalyst containing 14.12% by weight $MoO_3$, 1% by weight P, and 1% by weight CaO in the presence of octanol at a space velocity of 0.68/hr, temperature of 211° C., pressure of 44 bar and a mass ratio of 0.53 of octanol to soy oil to produce a crude product containing fatty acid octyl ether and glycerin. The reaction conditions were: The crude fatty acid octyl ester feedstock contained 98% fatty acid octyl ester and 2% monoglyceride.

Example 5

Continuous

An alumina supported catalyst (21.4 g) containing 14.9% by weight $MoO_3$ and 2.0% by weight P was positioned in a stainless steel fixed bed reactor (1.6 cm×36.5 cm). The crude soy methyl ester mixture from Example 3 and an excess of 1-octanol (molar ratio of crude soy methyl ester to octanol of 1:9) was contacted with the molybdenum catalyst at space velocities between of 0.4/hr and 0.75/hr temperature of 200° C. and a pressure of 1 atm. About 99.7% of the fatty acid methyl ester was converted to the octyl ester, as analyzed by HPLC. Methanol and the octyl esters were recovered by distillation.

Example 6

Continuous

An alumina supported catalyst (11.4 g) containing 14.9% by weight $MoO_3$ and 2.0% by weight P was positioned in a stainless steel fixed bed reactor (1.6 cm×36.5 cm). Crude sunflower methyl ester mixture was contacted with the catalyst in the presence of 2-ethyl-1-hexanol or 1-octanol a space velocity of 0.4/hr and 1 atm to produce the corresponding fatty acid alkyl esters. TABLE 2 lists the degree of conversion at varying temperatures.

TABLE 2

| Alcohol | Temp (° C.) | Ester Yield (%) | Mass Balance (%) |
| --- | --- | --- | --- |
| 1-Octanol | 230 | 90.3 | 87.9 |
| 1-Octanol | 230 | 93.5 | 97.8 |
| 2-Ethyl-1-hexanol | 230 | 93.5 | 97.8 |
| 2-Ethyl-1-hexanol | 240 | 93.3 | 97.7 |
| 2-Ethyl-1-hexanol | 250 | 92.5 | 97.4 |

Continuous. A tubular reactor with five sagitally positioned thermowells was equipped with thermocouples to measure temperatures throughout the length of catalyst bed. Mass flow meters were installed in-line to measure mass flow rates into the reactor for both feedstock and methanol and from the reactor and to adjust the mass ratios to control the process. The catalyst bed was formed by filling the space (0.304 m ID×2.134 mL) with 90.7 kg catalyst and a layer of inert alumina balls above (5.71 kg) and below (5.71 kg) the catalyst bed, the alumina balls serving as a support for the catalyst bed and space filling to reduce reactor void volume and to increase reagent and effluent flow rates through the reactor. These inert alumina balls had no catalytic properties under the process conditions described herein.

The feedstock was pumped into the reactor from the bottom of the reactor to the top of the reactor (upflow mode). The catalyst included about 15% by weight $MoO_3$, 3% by weight P, and 1% by weight CaO supported on alumina. The catalyst was prepared as described herein and in U.S. Pat. No. 8,124,801 to Srinivas et al.

The catalyst was activated by introducing a heated stream of dry nitrogen gas into the contacting zones at a space velocity of 500/hr (SV=vol $N_2$/hr divided by vol of catalyst) at atmospheric pressure. The temperature was increased from ambient temperature to 200° C. in the contacting zone (catalyst bed) at a rate of 50° C./hr and then held at 200° C. for 6 hrs. Following this holding period, the temperature was raised again to 25° C. at a rate of 50° C./hr and then held there for an additional 4 hrs. At the conclusion of this last holding period the flow rate of nitrogen was reduced to a space velocity of 5/hr and the catalyst bed permitted to cool to that start-up temperature of 150° C.

The crude feedstock (see, TABLE 3 for properties of feedstock) and the methanol (methanol, 99.95% purity) were pumped through an in-line static mixer and inline heater into the reactor.

The reactor pre-heater raised the temperature of the reagents to within 10° C. of the preferred reactor temperature. The reagent mixture flowed upwards through the contacting zone and out of the top of the reactor.

Normal contacting conditions were as follows: WHSV of 0.4 $h^{-1}$ (WHSV=0.4/hr, where WHSV=wt of oil/hr divided by wt of catalyst), an average temperature across the contacting zone ranged between 200-210° C., pressure of 46-55 bar and a molar ratio of methanol to feedstock in the range of 12 to 15:1. These operating conditions were controlled by a programmed logic system, which was designed to hold these parameters within a range of +/−3% of set point.

A total of 957.6 kg of feedstock was processed over a 24 hr period at the a WHSV of 0.45/hr, average catalyst bed temperature of 210° C., pressure of 47 bar and a molar ratio of 12:1. Upon exiting the reactor, the reactor pressure was reduced through a back pressure valve to 1-2 bar and the methanol, which flash evaporated, was recovered for recycle. The total raw/crude product was analyzed periodically after the methanol flash and conversion of corn oil into fatty acid methyl esters was 99.5% as determined by gas chromatography analysis using ASTM method D6584.

A total product exited the reactor (that is, crude product consisting of fatty acid methyl esters and some unreacted glycerides, water, methanol and glycerin) and passed through a high-pressure separator. In the high-pressure separator, a vacuum of 250-350 mmHg was applied at 100° C. to evaporate a significant portion of the methanol and water from the total product (95+% of methanol). This methanol and water vapor mixture are condensed elsewhere and stored for later refinement of the methanol.

The crude fatty acid alkyl ester/glycerin stream was introduced into an electrostatically enhanced gravity separator. In the electrostatic separator, the glycerin stream and the crude fatty acid methyl ester stream were separated continuously. Each separated phase was pumped to respective holding tanks. Separating conditions in the electrostatic precipitator were nominally: input voltage: 480 V, single phase, at 10.4 amp, secondary voltage: 23 kV, single phase at 217 amp, tertiary voltage: 100 V at 2 amp.

The crude fatty acid alkyl ester stream was purified using a short-path distillation system operating at between 24-30 mmHg with a jacket temperature of 200° C. to yield a clear, colorless, bright liquid. The distilled product was routinely analyzed by GC, HPLC and NIR to determine the purity of the distilled product and specification grade relative to ASTM standards. Crude product and distilled product composition and properties are summarized in Table 2. The distilled products met the ASTM specifications (ASTM Method D6751) for biodiesel.

The glycerin recovered from the electrostatic separator was assayed to be 93-97% pure within minor impurities only, methanol and water. Variations in crude glycerin composition are due to variations in the process. No further refinement of the glycerin was carried out in these Examples, as methods for glycerin refinement are known. Other embodiments of this general process may include vacuum distillation of the glycerin to achieve higher commercial grades.

Methanol recovered from the Flash apparatus is recycled through a distillation system with column employing a structured packing, a variable reflux ratio and a forced reboiler. The methanol recycle in the fashion afforded 99.5% recovery of unreacted methanol at a purity of 99.9% methanol and 0.1% water.

TABLE 4 lists the operating conditions, feed stock conversions, biodiesel yield, and glycerin yield for RBD soy oil, degummed soy, corn oil, poultry fat, bleachable fancy tallow, a yellow grease-soy blend, a 70:30 blend of degummed soy oil and pure oleic acid and the distillation bottoms using the process described in Example 7. The molar ratio was based on the original weight of triglyceride imputed to this sample of distillation bottoms.

In this patent, certain U.S. patents and U.S. patent applications have been incorporated by reference. The text of such U.S. patents and U.S. patent applications materials is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. In addition, it is to be understood that features described herein independently may, in certain embodiments, be combined.

TABLE 3

| Feedstock | Moisture (wt %) (AOCS Ca 2e-84) | Free Fatty Acid (wt %) (ASTM D664, B) | Unsaponifiables (AOCS 6b-53) |
| --- | --- | --- | --- |
| RBD Soy Oil (food grade) | 0.10 | 0.15 | 0.42 |
| Degummed Soy Oil | 0.08 | 0.15 | 0.50 |
| Corn Oil from EtOH DDGS* | 0.18 | 10.1 | 0.71 |
| Corn Oil from EtOH DDGS | 0.19 | 12.24 | 0.65 |
| Poultry Fat | 0.13 | 3.85 | 1.74 |
| Bleachable Fancy Tallow | 0.19 | 1.86 | 2.18 |
| Yellow Grease | 0.23 | 7.11 | 0.41 |

*DDGS refers to Distillers' dried grains and solubles.

TABLE 4

| | | Operating Conditions | | | | | |
| --- | --- | --- | --- | --- | --- | --- | --- |
| Example | Feedstock | Temp (° C.) | Press (bar) | WHSV (hr$^{-1}$) | Molar Ratio MeOH:feedstock | Feedstock Conv. | Biodiesel Yield (%) |
| 1.A | RBD Soy Oil | 200 | 47 | 0.4 | 15 | 99.9 | 99.7 |
| 1.B | Degummed Soy Oil | 185 | 54 | 0.5 | 15 | 97.5 | 99.0 |
| 1.C | Corn Oil | 185 | 43 | 0.5 | 15 | 98.4 | 99.4 |
| 1.D | Poultry Fat | 210 | 47 | 0.6 | 9 | 93.4 | 99.7 |
| 1.E | Bleachable Fancy Tallow | 199 | 39 | 0.45 | 9 | 95.9 | 99.5 |
| 1.F | Yellow Grease (1:1, w/w) | 190 | 37 | 0.4 | 15 | 96.0 | 99.1 |
| 1.G | Deg. Soy/Oleic acid (7:3, w/w) | 180 | 28 | 0.4 | 15 (soy); 8 (OA) | 97.1 | 99.8 |
| 2.A | Distillation Bottoms | 170 | 28 | 0.4 | 9 | 98.3 | 99.1 |

What is claimed is:

1. A method of continuous manufacture of a fatty acid $C_5$-$C_{50}$ alcohol ester comprising
   contacting a fatty acid methyl ester feedstock stream with a $C_5$-$C_{50}$ alcohol stream with a hexavalent molybdenum catalyst to produce a reaction mixture stream comprising a fatty acid $C_5$-$C_{50}$ alcohol ester, wherein the hexavalent molybdenum catalyst is present in an amount in the range of about 5% to about 20% by weight; and
   flash distilling the fatty acid alcohol ester reaction mixture stream to separate one or more distillates from the $C_5$-$C_{50}$ alcohol ester reaction mixture stream.

2. The method of claim 1 wherein the hexavalent molybdenum catalyst comprises molybdenum trioxide.

3. The method of claim 1 further comprising a promoter.

4. The method of claim 3 wherein the promoter comprises one or more elements from Group VIB of a periodic table.

5. The method of claim 3 wherein the promoter is present in an amount in the range of about 0.1% to about 0.7% by weight of the catalyst.

6. The method of claim 1 further comprising a co-promoter.

7. The method of claim 6 wherein the co-promoter comprises one or more elements from Group IA, Group IIA, Group IIIB, or Group VIII of a periodic, table, or mixtures thereof.

8. The method of claim 6 wherein the co-promoter is present in an amount in the range of about 0.0001% to about 10% by weight of the catalyst.

9. The method of claim 1 wherein the catalyst, promoter, co-promoter, or mixture thereof is supported by a solid support comprising a refractory metal oxide wherein the metal comprises a member of Group IIIA of a periodic table.

10. The method of claim 1 wherein the surface area of the catalyst comprises a range between 50 $m^2/g$ to 300 $m^2/g$.

11. The method of claim 1 wherein the catalyst comprises a pore volume ranging from 0.2 ml/g to 0.95 ml/g.

12. The method of claim 1 wherein the catalyst is calcined at a temperature in the range of about 100° C. to about 600° C. for a time ranging from 0.5 hours to 48 hours.

13. The method of claim 1 further comprising a double metal cyanide catalyst.

14. The method of claim 1 wherein the fatty acid methyl ester feedstock is pre-incubated with a $C_5$-$C_{50}$ alcohol prior to the addition of the catalyst.

15. The method of claim 1 wherein the catalyst is pre-activated by heating or drying prior to contacting the fatty acid methyl ester feedstock stream and the $C_5$-$C_{50}$ alcohol stream.

16. The method of claim 1 wherein a reaction temperature comprises a range of about 165° C. to about 260° C. and wherein a reaction pressure comprises about 0.21MPa to about 5.5 MPa.

17. The method of claim 1 further comprising electrostatically separating the fatty acid $C_5$-$C_{50}$ alcohol ester reaction mixture stream to separate one or more distillates from the $C_5$-$C_{50}$ alcohol ester reaction mixture.

18. The method of claim 1 wherein the hexavalent molybdenum catalyst comprises a fixed bed catalyst.

* * * * *